United States Patent
Yogo

(10) Patent No.: US 12,201,359 B2
(45) Date of Patent: Jan. 21, 2025

(54) OCT APPARATUS

(71) Applicant: NIDEK CO., LTD., Aichi (JP)

(72) Inventor: Hirofumi Yogo, Aichi (JP)

(73) Assignee: NIDEK CO., LTD., Aichi (JP)

( * ) Notice: Subject to any disclaimer, the term of this patent is extended or adjusted under 35 U.S.C. 154(b) by 435 days.

(21) Appl. No.: 17/707,305

(22) Filed: Mar. 29, 2022

(65) Prior Publication Data

US 2022/0313079 A1    Oct. 6, 2022

(30) Foreign Application Priority Data

Mar. 30, 2021    (JP) .................................. 2021-057158

(51) Int. Cl.
*A61B 3/10*    (2006.01)
*A61B 3/00*    (2006.01)

(52) U.S. Cl.
CPC ............ *A61B 3/102* (2013.01); *A61B 3/0025* (2013.01)

(58) Field of Classification Search
CPC .............................. A61B 3/102; A61B 3/0025
USPC ......................................................... 351/206
See application file for complete search history.

(56) References Cited

U.S. PATENT DOCUMENTS

| | | |
|---|---|---|
| 2012/0083667 A1 | 4/2012 | Isogai et al. |
| 2014/0268038 A1 | 9/2014 | Schmoll |
| 2015/0094978 A1 | 4/2015 | Hanebuchi et al. |
| 2015/0327762 A1 | 11/2015 | Isogai et al. |
| 2015/0369586 A1 | 12/2015 | Fukuhara et al. |
| 2017/0280993 A1* | 10/2017 | Fukuhara ................ A61B 3/102 |
| 2018/0028056 A1* | 2/2018 | Kubota ....................... G06T 7/12 |
| 2018/0135962 A1 | 5/2018 | Murata et al. |
| 2020/0397282 A1* | 12/2020 | Hirose .................... A61B 3/102 |
| 2021/0093186 A1* | 4/2021 | Shiba ...................... A61B 3/102 |

FOREIGN PATENT DOCUMENTS

| | | |
|---|---|---|
| JP | 201275640 A | 4/2012 |
| JP | 2015-68775 A | 4/2015 |
| JP | 2016-2381 A | 1/2016 |
| JP | 2018-63193 A | 4/2018 |
| JP | 2018124188 A | 8/2018 |

OTHER PUBLICATIONS

Office Action issued on Oct. 1, 2024 by the Japan Patent Office in counterpart Japanese Patent Application No. 2021-057158.

* cited by examiner

*Primary Examiner* — Mohammed A Hasan
(74) *Attorney, Agent, or Firm* — Sughrue Mion, PLLC

(57) ABSTRACT

An OCT apparatus has a wavelength sweep light source changing a sweep frequency between a first sweep frequency and a second sweep frequency, an OCT optical system, an image processor, an FPN generation optical system generating a first FPN and a second FPN generated at a position separated from a zero delay position with respect to the first FPN, a detector, and a controller. The controller acquires first correction information based on the first FPN detected in a case of the first sweep frequency, and second correction information based on the second FPN detected in a case of the second sweep frequency. The controller applies the first correction information to an arithmetic process on a spectral interference signal obtained in the case of the first sweep frequency, and the second correction information to the arithmetic process on the spectral interference signal obtained in the case of the second sweep frequency.

7 Claims, 17 Drawing Sheets

(SWEEP FREQUENCY : H1)

(SWEEP FREQUENCY : H1)

FIG. 8A  (SWEEP FREQUENCY : H1)
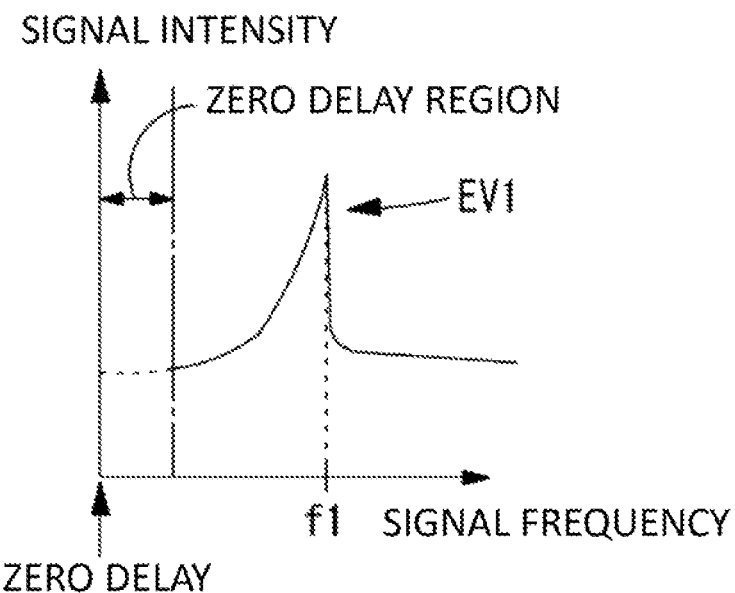
FIG. 8B  (SWEEP FREQUENCY : H2)
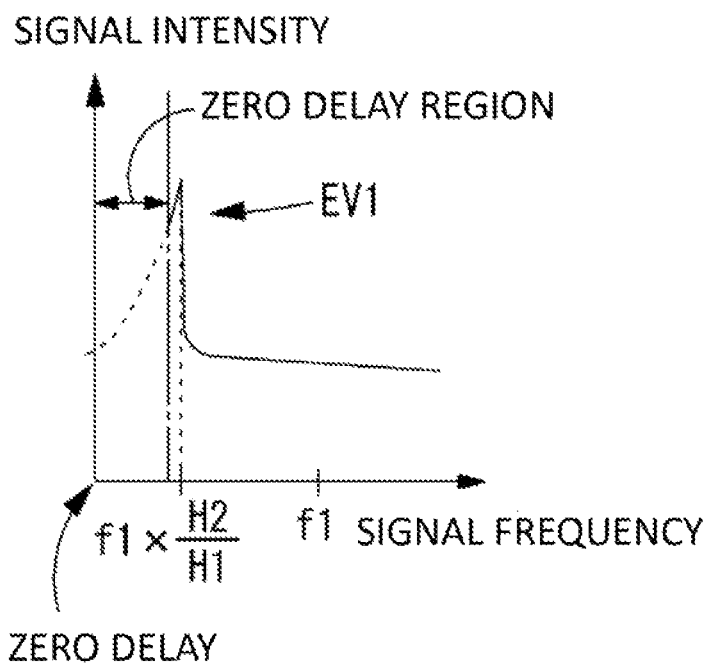

FIG. 12A  CORRECTION OF SLOPE
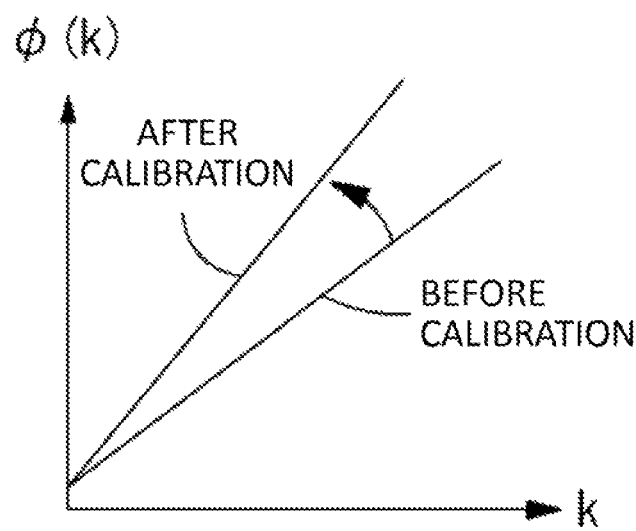
FIG. 12B  CORRECTION OF DEVIATION
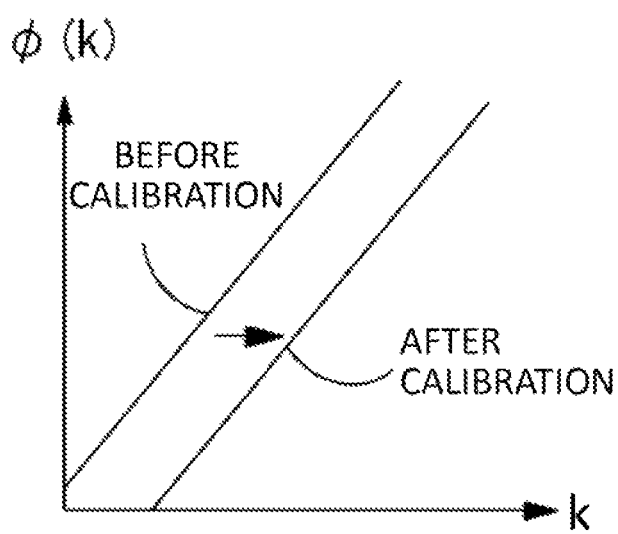

OCT APPARATUS

CROSS-REFERENCE TO RELATED APPLICATION

This application claims priority from Japanese Patent Application No. 2021-057158 filed on Mar. 30, 2021, the entire subject-matter of which is incorporated herein by reference.

TECHNICAL FIELD

The present disclosure relates to an OCT apparatus that obtains OCT data of a subject eye.

BACKGROUND

In recent years, swept source OCT (SS-OCT) is being utilized in the field of ophthalmology. The SS-OCT is provided with a wavelength sweep light source as an OCT light source, and acquires OCT data by sampling a spectral interference signal between a measurement light and a reference light guided to tissue of a subject eye at high speed and further processing the resultant signal.

In such an apparatus, a mapping state between the spectral interference signal obtained by sampling and a wavenumber space is affected by changes over time or environmental changes of the apparatus and is changed from an initial state. Accordingly, calibration is performed as appropriate. For example, JP-A-2018-124188 discloses an apparatus including a fixed pattern noise (FPN) generating optical system having an optical member for generating an FPN signal, and performing calibration on a wavenumber component by using the FPN signal.

Further, in the technical field of the SS-OCT, there is proposed an apparatus capable of changing a sweep frequency in a wavelength sweep light source. For example, JP-A-2012-075640 disclose an apparatus capable of significantly changing an imaging range in a depth direction from the extent that a local portion (anterior eyes or fundus) of a subject eye can be imaged to the extent that the entire eyeball (from cornea to fundus) can be imaged, by changing a sweep frequency. Further, it is considered that a sensitivity, an imaging time of A scan, and the like are also changed by changing the sweep frequency.

However, when an FPN generation optical system suitable for calibration at a constant sweep frequency is applied to the apparatus of which the sweep frequency can be changed as in JP-A-2018-124188, an appropriate FPN signal may not be acquired in some cases. For example, in a case where the sweep frequency is reduced while keeping an optical distance between a position corresponding to a zero delay position and a position of the optical member that generates FPN constant, an envelope of a peak formed when the FPN signal is Fourier transformed may enter a zero delay region. In such a case, appropriate calibration data cannot be acquired.

SUMMARY

A technical object of the present disclosure is to provide an OCT apparatus capable of appropriately acquiring OCT data.

An aspect of the present disclosure is an OCT apparatus including:
a wavelength sweep light source configured to change a sweep frequency between a first sweep frequency and a second sweep frequency smaller than the first sweep frequency;
an OCT optical system including:
a light splitter that divides light from the wavelength sweep light source into measurement light and reference light; and
a first detector that detects a spectral interference signal between the measurement light guided to tissue of a subject eye and the reference light;
an image processor that performs an arithmetic process on the spectral interference signal to acquire OCT data of the subject eye;
an FPN generation optical system including at least one optical member that generates a first FPN and a second FPN generated at a position separated from a zero delay position with respect to the first FPN;
a second detector that detects FPNs including the first FPN and the second FPN; and
a computation controller configured to:
acquire first correction information based on at least the first FPN detected in a case where the sweep frequency is the first sweep frequency, and acquire second correction information based on at least the second FPN detected in a case where the sweep frequency is the second sweep frequency, the first correction information and the second correction information being information for correcting a mapping state of a wavenumber component; and
apply the first correction information to the arithmetic process on the spectral interference signal obtained in the case of the first sweep frequency, and apply the second correction information to the arithmetic process on the spectral interference signal obtained in the case of the second sweep frequency.

BRIEF DESCRIPTION OF DRAWINGS

FIGS. 8A and 8B are diagrams describing that a signal frequency at which the FPN signal is detected is changed depending on a sweep frequency.

FIGS. 12A and 12B are diagrams illustrating that the correspondence deviation is corrected by the calibrated correction information.

DETAILED DESCRIPTION

Overview

Figure 1:
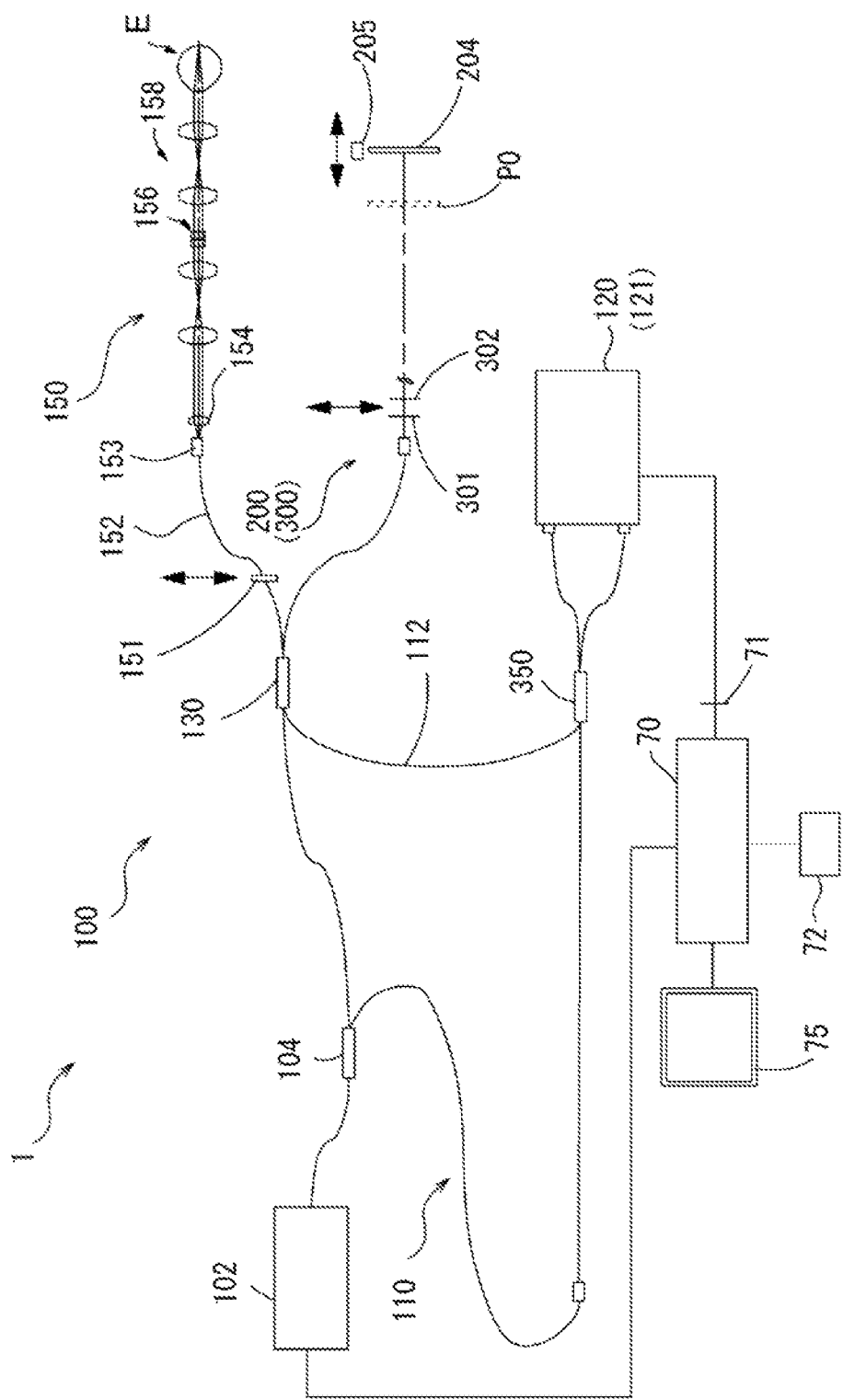
FIG. 1 is a diagram illustrating an example of an OCT apparatus according to the present embodiment.

An embodiment of the present disclosure will be described. Items classified by < and > below may be used independently or in relation to each other. For example, in one embodiment, a plurality of items can be appropriately combined. Further, for example, the items described for one embodiment can be applied to other embodiments.

For example, the invention described in a first embodiment and the invention described in a second embodiment may be implemented at the same time. Further, any of the invention described in the first embodiment and the invention described in the second embodiment may be implemented.

First Embodiment

In an OCT apparatus according to the first embodiment, calibration data corresponding to each sweep frequency is appropriately acquired in the apparatus capable of changing a sweep frequency to a plurality of frequencies.

The OCT apparatus according to the first embodiment may include an OCT optical system, and can acquire OCT data by arithmetically processing a spectral interference signal output from a first detector of the OCT optical system with an image processor.

<OCT Optical System>

The OCT optical system may be, for example, a Fourier domain OCT optical system. For example, the OCT apparatus may be a wavelength sweep type OCT (swept source OCT (SS-OCT)).

The OCT optical system may divide light emitted from a wavelength sweep light source into measurement light and reference light with a light splitter. Further, the OCT optical system may detect a spectral interference signal of a reflected light of the measurement light from a subject eye and the reference light with a first detector.

For example, the wavelength sweep light source may be a wavelength sweep light source of which a sweep frequency can be changed between a first sweep frequency and a second sweep frequency smaller (lower) than the first sweep frequency. In the present embodiment, the sweep frequency indicates the number of times a sweep is performed per unit time. For example, an imaging range of the OCT apparatus in a depth direction may be changed by changing between the first sweep frequency and the second sweep frequency. For example, the first sweep frequency may be a sweep frequency for acquiring a tomographic image of a fundus of the subject eye, and the second sweep frequency may be a sweep frequency for acquiring a tomographic image of the entire eyeball of the subject eye. Further, an imaging time or a sensitivity of measurement may be changed, by changing the sweep frequency between the first sweep frequency and the second sweep frequency. For example, the OCT apparatus may selectively set a first imaging mode for imaging at the first sweep frequency or a second imaging mode for imaging at the second sweep frequency.

<FPN Generation Optical System>

The OCT apparatus may include an FPN generation optical system. The FPN generation optical system may be, for example, an optical system including an optical member for generating a first FPN and a second FPN, and a second detector capable of detecting the first FPN signal and the second FPN signal. In the first embodiment, in a case of the same condition of a sweep frequency, a position at which the second FPN is generated is a position farther from a zero delay position than a position of the first FPN. In the present embodiment, the zero delay position is a depth position of an OCT image at which optical path lengths of measurement light and reference light coincide with each other.

Further, a part of the configuration is used in common between the FPN generation optical system and the OCT optical system. For example, the second detector of the FPN generation optical system is also used as the first detector of the OCT optical system. That is, the FPN generation optical system guides light from a light source to the optical member for generating an FPN, and guides the light via the optical member to the first detector.

The OCT apparatus may be provided with a drive unit that changes an optical distance between a position corresponding to the zero delay position and a position of the optical member. In the present embodiment, the position corresponding to the zero delay position is a position at which an optical path length from the light source to incident on the detector via the optical member and an optical path length of a reference optical path coincide with each other, in a case where the optical member is disposed. That is, the position corresponding to the zero delay is a position at which the FPN is generated at the zero delay position, in a case where the optical member is disposed. In the present embodiment, the position corresponding to the zero delay position is referred to as an origin position.

For example, the drive unit changes an optical path length of the FPN generation optical system or an optical path length of the reference optical path to change an optical distance. For example, the drive unit may change an optical distance between a first distance at which the first FPN is generated and a second distance at which the second FPN is generated. For example, the drive unit may change the optical distance to the first distance in a case where a wavelength sweep light source has a first sweep frequency and to the second distance in a case where the wavelength sweep light source has a second sweep frequency.

In addition, in the FPN generation optical system, for example, a first optical member for generating a first FPN is provided. Further, in the FPN generation optical system, for example, a second optical member for generating a second FPN is provided. For example, the first optical member and the second optical member are used in common.

For example, the first optical member and the second optical member may be separate members. In that case, the first optical member and the second optical member may be arranged such that an optical distance from an origin position to the second optical member is longer than an optical distance from the origin position to the first optical member.

<Correction in Mapping State>

The OCT apparatus may be provided with a computation controller that obtains correction information for correcting a mapping state of a wavenumber component. The computation controller may acquire first correction information based on a first FPN. For example, in a case of a first sweep frequency, the computation controller performs an arithmetic process on a spectral interference signal, by using the first correction information. As a result, in the case of the first sweep frequency, the mapping state of the wavenumber component is corrected. For example, the mapping state of the wavenumber component is corrected so that a correspondence between a sampling point and a wavenumber of light ($2\pi/\lambda$, $\lambda$ is a wavelength of light) becomes linear (see FIG. 4).

In the same manner, the computation controller may acquire second correction information based on a second FPN. Further, in a case of a second sweep frequency, the computation controller performs the computation process on the spectral interference signal, by using the second correction information. As a result, in the case of the second sweep frequency, the mapping state of the wavenumber component is corrected.

For example, the computation controller may acquire correction information in advance before acquiring OCT data of the subject eye.

Further, for example, the FPN generation optical system may generate a third FPN in a case where a wavelength sweep light source has the first sweep frequency, and may generate a fourth FPN in a case where the wavelength sweep light source has the second sweep frequency. For example, when a position of the first FPN and a position of the third FPN are compared under the same condition of a sweep frequency, the third FPN may be generated so that the position of the first FPN and the position of the third FPN are different from each other. In addition, the same applies to a relationship between the second FPN and the fourth FPN.

In this case, for example, the computation controller may acquire the first correction information, based on difference information between mapping information of the wavenumber component based on the first FPN and mapping information of the wavenumber component based on the third FPN. Further, the second correction information may be acquired based on difference information between mapping information of the wavenumber component based on the second FPN and mapping information of the wavenumber component based on the fourth FPN. According to this, a dispersion component included in the mapping state of the wavenumber component can be corrected (see FIGS. 3A and 3B).

Further, the computation controller may acquire the correction information in a state where measurement light is intercepted. In this case, for example, an interception member for intercepting the measurement light may be detachably provided in the OCT optical system. For example, the computation controller acquires the first correction information, based on the first FPN detected by the second detector, in a state in which the interception member is inserted in the OCT optical system. In the same manner, for example, the computation controller acquires the second correction information, based on the second FPN detected by the second detector, in a state in which the interception member is inserted in the OCT optical system.

With the above configuration, for example, even in a case where the wavelength sweep light source changes the sweep frequency, the FPN signal can be appropriately acquired, by changing a signal frequency at which the FPN is detected.

For example, in the present embodiment, an electrical filter that cuts a DC component is provided between the detector and the computation controller to protect the computation controller. In the present embodiment, a region of the frequency cut by this electrical filter is referred to as a zero delay region. For example, in the present embodiment, the FPN can be generated at a signal frequency at which an envelope of a peak formed during the Fourier transform does not fall into the zero delay region.

Therefore, the correction information can be appropriately acquired by using the generated FPN. Therefore, the OCT data can be appropriately acquired.

Further, for example, the FPN generation optical system may include a light intensity regulator. For example, the light intensity regulator adjusts an intensity of light emitted from the FPN generation optical system, based on the sweep frequency of the wavelength sweep light source. For example, the light intensity regulator adjusts the intensity of the light so that the FPN signal is within a dynamic range of the first detector. According to this, even in a case where the sweep frequency is changed and the intensity of the light from the wavelength sweep light source is changed, the first detector can appropriately detect the FPN signal.

Second Embodiment

In an OCT apparatus according to the second embodiment, a correspondence deviation between a time and a wavenumber when a wavelength sweep light source sweeps a wavelength is appropriately corrected.

The OCT apparatus according to the second embodiment includes an OCT optical system. The OCT optical system described in the first embodiment is also incorporated in the second embodiment.

<Computation Controller>

The OCT apparatus may include a computation controller that arithmetically processes a detected spectral interference signal, and acquires OCT data of a subject eye. Further, the computation controller may correct a deviation in correspondence between a time and a wavenumber (hereinafter, referred to as a correspondence deviation), for light emitted from a wavelength sweep light source. For example, by correcting the correspondence deviation, a slope of a graph in a mapping state of a wavenumber component is corrected (see FIG. 12A). Further, by correcting the correspondence deviation, a shift (parallel translation) of the graph of the mapping state of the wavenumber component is corrected (see FIG. 12B).

<Calibration Optical System>

The OCT apparatus may include a calibration optical system for correcting a correspondence deviation. The calibration optical system has a wavelength-selective wavelength extraction member that extracts light having a predetermined wavelength, from light included in a sweep range of a wavelength sweep light source. For example, the calibration optical system detects light having the predetermined wavelength from light swept by the wavelength sweep light source via the wavelength extraction member.

For example, the wavelength-selective wavelength extraction member may be detachably provided in the calibration optical system. For example, in the present embodiment, a spectral interference signal detected by the computation controller in a state in which the wavelength extraction member is inserted into the calibration optical system is used as a calibration interference signal. The computation controller may correct the correspondence deviation based on a predetermined wavelength detection timing in the calibration interference signal.

The wavelength extraction member is retracted with respect to an optical axis, except when the correction interference signal is acquired to correct the correspondence deviation.

For example, the OCT apparatus may be provided with a light guide optical system that guides measurement light to a subject eye.

For example, at least one of the FPN generation optical system and the light guide optical system, and the calibration optical system may be partially used as a part of the optical system. In that case, at least one of the FPN generation optical system and the light guide optical system is provided with the wavelength extraction member.

For example, the calibration optical system acquires the calibration interference signal to be used to correct the correspondence deviation. For example, the calibration interference signal is a spectral interference signal, acquired by a detector from a start to an end of the sweep of the wavelength sweep light source, by light from the wavelength sweep light source via the wavelength extraction member and a reference light. For example, in the calibration interference signal, a spectral interference signal is generated by light having a predetermined wavelength and the reference light at a sampling point corresponding to a timing at which the wavelength sweep light source emits light having the predetermined wavelength. For example, the members of the calibration optical system and the OCT optical system may be partially used in common. For example, the detector provided in the calibration optical system and the detector provided in the OCT optical system may be used in common. In that case, the calibration optical system guides the light having the predetermined wavelength via the wavelength extraction member to the detector of the OCT optical system.

<Removal of Correspondence Deviation (Calibration)>

In the present embodiment, a sampling point at which a spectral interference signal by light having a predetermined wavelength and reference light in a calibration interference signal is detected is referred to as a detection timing. For example, the computation controller processes the calibration interference signal to acquire the detection timing. For example, the computation controller calibrates correction information for correcting a mapping state of a wavenumber component based on the detection timing. For example, the computation controller performs an arithmetic process and corrects the mapping state of the wavenumber component by using the calibrated correction information to correct a correspondence deviation included in the mapping state of the wavenumber component. In the present disclosure, the arithmetic process for calibrating the correction information is referred to as a calibration process.

For example, a wavelength extraction member, provided in a calibration optical system, for extracting light having a predetermined wavelength may be a wavelength extraction member which can extract light having a predetermined first wavelength and light having a second wavelength different from the first wavelength. In this case, the computation controller may calibrate the correction information by using a detection timing at which the light of the first wavelength is detected and a detection timing at which the light of the second wavelength is detected. According to this, in a case where the mapping state of the wavenumber component is corrected, the correction information can be calibrated so that the correspondence deviation is corrected.

For example, the calibration of the correction information may be performed before acquiring OCT data of a subject eye. In this case, the correction information based on an FPN may be acquired and the correction information based on the detection timing may be calibrated before the OCT data of the subject eye is acquired.

For example, the OCT apparatus may include changing means that changes an optical path length difference of a measurement optical path through which measurement light passes and a reference optical path through which reference light passes between a predetermined first optical path length difference and second optical path length difference.

For example, the changing means may change an optical path length of the FPN generation optical system. Further, the changing means may change an optical path length of the reference optical system. For example, the changing means changes the optical path length difference by changing at least one optical path length of the optical path length of the FPN generation optical system and the optical path length of the reference optical system.

For example, the computation controller may correct the correspondence deviation, based on a predetermined wavelength detection timing in a case where the optical path length difference is the first optical path length difference, and a predetermined wavelength detection timing in a case where the optical path length difference is the second optical path length difference. For example, the computation controller adds an interference signal acquired in a case where the optical path length difference is the first optical path length difference and an interference signal acquired in a case where the optical path length difference is the second optical path length difference. According to this, a signal intensity of the spectral interference signal generated at the predetermined wavelength detection timing is increased. Therefore, the computation controller can more accurately acquire the predetermined wavelength detection timing.

That is, the computation controller may correct the correspondence deviation, by performing the calibration process using a calibration interference signal detected by the detector when the optical path length difference is the first optical path length difference and a calibration interference signal detected by the detector when the optical path length difference is the second optical path length difference.

With the above configuration, for example, regarding the light of the wavelength sweep light source, the deviation in correspondence between the time and the wavenumber can be appropriately corrected, so that the OCT data of the subject eye can be appropriately acquired.

Embodiment

Examples of the embodiments of the present disclosure will be described with reference to the drawings. FIGS. 1 to 13 are diagrams according to the examples of the first and second embodiments. Items classified by < and > below may be used independently or in relation to each other.

<OCT Optical System>

In the present embodiment, an optical coherence tomography (OCT) apparatus illustrated in FIG. 1 is used as an OCT apparatus 1. The OCT apparatus 1 according to the present embodiment includes, for example, a wavelength sweep type OCT (swept source-OCT (SS-OCT)) as a basic configuration, and includes a wavelength sweep light source 102, an OCT optical system 100, and a computation controller (computation control unit, and also referred to as a control unit below) 70. In addition, the OCT apparatus 1 includes a memory 72, a display unit 75, and a front image observation system and a fixation target projection system (not illustrated). The control unit 70 is connected to the wavelength sweep light source 102, the OCT optical system 100, the memory 72, and the display unit 75.

The OCT optical system 100 guides measurement light to a subject eye E by a light guide optical system 150. The OCT optical system 100 guides reference light to a reference optical system 110. The OCT optical system 100 causes a detector (light reception element) 120 to receive interference signal light acquired by interference between the measurement light reflected by the subject eye E and the reference light. Further, the OCT optical system 100 of the present embodiment includes an FPN generation optical system 200 (details will be described below). In addition, the OCT optical system 100 includes a calibration optical system 300 (details will be described below). In the present embodiment, the FPN generation optical system 200 and the calibration optical system 300 are used in common. The OCT optical system 100 may be mounted in a housing (apparatus body) (not illustrated), and the housing may be three-dimensionally moved with respect to the subject eye E by a well-known alignment movement mechanism via an operation member such as a joystick, so that the alignment with respect to the subject eye E may be performed.

An SS-OCT method is used for the OCT optical system 100, and a variable wavelength light source (wavelength scanning type light source) that changes an emission wavelength at high speed in time is used as the wavelength sweep light source 102. The wavelength sweep light source 102 is configured with, for example, a laser medium, a resonator, and a wavelength selection filter. As the wavelength selection filter, for example, a combination of a diffraction grating and a polygon mirror, and a filter using Fabry-Perot Etalon are used.

Further, in the present embodiment, the wavelength sweep light source 102 can change a sweep frequency. In the present embodiment, the sweep frequency indicates the number of times a sweep is performed per unit time. For example, the wavelength sweep light source 102 can change the sweep frequency between a predetermined first sweep frequency H1 (for example, 200 kHz) and a predetermined second sweep frequency H2 (for example, 25 kHz). The number of sweep frequencies that can be changed is not limited to two.

For example, by changing the sweep frequency by the wavelength sweep light source 102, an imaging range of the OCT apparatus 1 is changed in a depth direction.

A coupler (splitter) 104 is used as a light splitter, and divides light emitted from the wavelength sweep light source 102 into a measurement optical path and a reference optical path. For example, the coupler 104 guides the light from the wavelength sweep light source 102 to an optical fiber 105 on the measurement optical path side, and also guides the light to the reference optical system 110 on the reference optical path side.

The coupler (splitter) 130 divides the light (measurement light) from the optical fiber 105 into an optical path of the light guide optical system 150 and an optical path of the FPN generation optical system 200. That is, the measurement optical path is provided with the light guide optical system 150 and the FPN generation optical system 200. The coupler (splitter) 130 may be a beam splitter, or may be a circulator.

<Light Guide Optical System>

The light guide optical system 150 is provided to guide the measurement light to the subject eye E. The light guide optical system 150 may be sequentially provided with, for example, an optical fiber 152, a coupler 153, a collimator lens 154, an optical scanner 156, and an objective lens system 158. In this case, the measurement light becomes a parallel beam by the collimator lens 154 via the optical fiber 152 and the coupler 153, and is directed to the optical scanner 156. The subject eye E is irradiated with the light passing through the optical scanner 156, via the objective lens system 158. Both the anterior and posterior eyes are irradiated with the measurement light, and the measurement light is scattered and reflected by each tissue.

The optical scanner 156 may scan the measurement light in an XY direction (transverse direction) on the subject eye E. The optical scanner 156 is, for example, two galvano mirrors, and a reflection angle thereof is freely adjusted by a drive mechanism. A luminous flux emitted from the wavelength sweep light source 102 changes its reflection (traveling) direction, and is scanned in any direction on the fundus. As the optical scanner 156, for example, a reflection mirror (galvano mirror, polygon mirror, and resonant scanner), an acoustic optical element (AOM) that changes the traveling (deflection) direction of light, or the like may be used.

In this case, the scattered light (reflected light) from the subject eye E by the measurement light passes through the objective lens system 158, the optical scanner 156, the collimator lens 154, the coupler 153, the optical fiber 152 to the coupler 130, and an optical fiber 112, and then reaches the coupler 350. The scattered light is combined with and interferes with the reference light in the coupler 350.

Further, for example, a shutter 151 may be detachably provided with respect to an optical axis, in the light guide optical system 150. For example, the shutter 151 is inserted with respect to the optical axis when correction information which will be described below is acquired.

The shutter 151 is an example of an interception member for intercepting light derived from the light guide optical system 150, and is not limited thereto. For example, a light absorption member may be provided as the interception means. In that case, for example, the control unit 70 controls the optical scanner 156 to guide light incident on the light guide optical system 150 (or returned light from the subject eye) to the light absorption member, so that the light derived from the light guide optical system 150 can be blocked.

<Reference Optical System>

The reference optical system 110 generates a reference light to be combined with the reflected light acquired by the reflection of the measurement light from the subject eye E. The reference light passing through the reference optical system 110 is combined with light from the measurement optical path by the coupler 350, and interferes with the light. The reference optical system 110 may have a Michaelson type or a Mach Zenda type.

An optical member for adjusting an optical path length difference between the measurement light and the reference light may be disposed in at least one of the measurement optical path and the reference optical path. For example, by integrally moving the collimator lens 154 and the coupler 153, an optical path length of the measurement light may be adjusted, and as a result, the optical path length difference between the measurement light and the reference light may be adjusted. Of course, by moving the optical member disposed in the reference optical path, the optical path length difference between the measurement light and the reference light may be adjusted, as a result.

<Detector>

The detector 120 is provided for detecting interference between light from the measurement optical path and light from the reference optical path. The detector 120 may perform equilibrium detection. In this case, the detector 120 includes a plurality of light reception elements, obtains a difference between an interference signal from a first light reception element and an interference signal from a second light reception element, and reduces unnecessary noise included in the interference signal. Each light reception element is a point sensor having only one light reception unit, and for example, an avalanche photodiode is used.

<FPN Generation Optical System>

The FPN generation optical system 200 generates an FPN signal. The FPN signal is used to correct mapping information of a wavenumber component. In the present embodiment, the FPN generation optical system generates a first FPN signal, a second FPN signal, a third FPN signal, and a fourth FPN signal.

As illustrated in FIG. 1, in the present embodiment, the FPN generation optical system 200 is disposed at a position to be branched with the light guide optical system 150, from the coupler (splitter) 130.

For example, the FPN generation optical system 200 includes an FPN generation member 204 for generating an FPN, a drive unit 205 for moving a position of the FPN generation member 204 in an optical axis direction, and a detector 121 for detecting an FPN. The FPN generation member 204 is an optical member for generating the FPN, and is, for example, a gold mirror. Further, the detector 121 for detecting the FPN is also used as the detector 120 provided in the OCT optical system 100.

For example, an FPN signal is generated when light incident on the FPN generation optical system 200 and passing through the FPN generation member 204 interferes with reference light. The generated FPN signal is detected by the detector 120. Further, the control unit 70 (which also serves as an image processor), which will be described below, generates an FPN on an OCT image based on the FPN signal.

For example, in the present embodiment, the FPN generation optical system 200 can change a position in a depth direction in which the FPN is generated on the OCT image.

For example, the drive unit 205 moves the FPN generation member 204 in a direction parallel to the optical axis. As a result, an optical distance from an origin position P0 to the FPN generation member 204 is changed. In the present embodiment, the origin position P0 is a position on the optical system in which the FPN is generated at a zero delay position on the OCT image in a case where the FPN generation member 204 is disposed.

Since the drive unit 205 changes the position of the FPN generation member 204, an optical path length of the FPN generation optics 200 is changed, so that an optical path length difference between the reference optical system 110 and the FPN generation optical system 200 is changed. The position in the depth direction in which the FPN is generated on the OCT image is changed depending on the optical path length difference between a reference optical path and the FPN generation optical system. From this, the drive unit 205 can change the position in the depth direction in which the FPN is generated by changing the position of the FPN generation member 204.

As compared with [Modification Example] (see FIG. 15) which will be described below, the optical path length of the FPN generation optical system 200 can be changed without dividing the optical path, so that there is a possibility that each FPN signal is strong and easy to detect. Further, since a plurality of FPN signals are not generated on the OCT image at the same time, there is a possibility that the arithmetic process performed by the control unit 70 is easy.

For example, in the present embodiment, the FPN generation optical system 200 can generate FPN signals in at least four different depth positions. The FPN signal is used in a case of acquiring correction information for correcting the mapping state of the wavenumber component described below.

<Calibration Optical System>

In the present embodiment, the calibration optical system 300 is used to correct a deviation in correspondence between a wavelength and a time of the wavelength sweep light source 102. In the present embodiment, the deviation in correspondence between the wavenumber and the time of the wavelength sweep light source 102 is referred to as a correspondence deviation.

As illustrated in FIG. 1, for example, the calibration optical system 300 detachably includes a bandpass filter 301 and a notch filter 302 with respect to an optical axis. The bandpass filter 301 and the notch filter 302 are examples of wavelength-selective wavelength extraction members that extract light having a predetermined wavelength included in a sweep range of the wavelength sweep light source 102.

For example, the bandpass filter 301 passes the above-described light having the predetermined wavelength in a wavelength bandwidth. For example, the notch filter 302 attenuates light in a part of the wavelength bandwidth passed by the bandpass filter 301. For example, the notch filter 302 attenuates light having a wavelength other than the light having the predetermined wavelength, among light passing through the bandpass filter 301. Therefore, by using the bandpass filter 301 and the notch filter 302 in combination, the light having the predetermined wavelength is selectively extracted.

Further, the bandpass filter 301 and the notch filter 302 are examples of wavelength extraction members for extracting the light having the predetermined wavelength, and the present invention is not limited thereto. For example, the same effect can be obtained by using a fiber Bragg grating as a wavelength extraction member for extracting light having a predetermined wavelength. In that case, by switching between an optical path provided with a fiber Bragg grating and an optical path not provided with the fiber Bragg grating, it is possible to switch whether or not light having a predetermined wavelength is extracted.

For example, in the present embodiment, in a case where the wavelength sweep light source 102 performs a sweep, the bandpass filter 301 and the notch filter 302 extract light having a predetermined first wavelength and light having a second wavelength different from the light having the first wavelength.

For example, in the present embodiment, the FPN generation optical system 200 and the calibration optical system 300 are used in common. Instead of this, the calibration optical system 300 may also be used as the light guide optical system 150. In this case, the bandpass filter 301 and the notch filter 302 are detachably provided in the light guide optical system 150.

For example, the bandpass filter 301 and the notch filter 302 are inserted with respect to an optical axis when acquiring a calibration interference signal, which will be described below. For example, the bandpass filter 301 and the notch filter 302 are retracted with respect to the optical axis except when acquiring the calibration interference signal.

The calibration optical system 300 may be provided in an optical path independent of the other optical systems. In that case, the bandpass filter 301 and the notch filter 302 do not necessarily have to be detachably provided.

<Control Unit>

As illustrated in FIG. 1, the control unit 70 may include a CPU (processor), a RAM, a ROM, and the like. For example, the CPU of the control unit 70 may control the OCT apparatus 1. The RAM temporarily stores various types of information. Various programs for controlling an operation of the OCT apparatus 1, initial values, and the like may be stored in the ROM of the control unit 70.

The non-volatile memory (hereinafter, abbreviated as memory) 72, a display unit 75, and the like may be electrically connected to the control unit 70. For the memory 72, a non-transient storage medium capable of holding storage contents even when power supply is cut off may be used. For example, a hard disk drive, a flash ROM, a USB memory detachably attached to the OCT apparatus 1, and the like can be used as the memory 72. The memory 72 may store a control program for controlling acquisition of OCT data and capturing of an OCT image. Further, in the memory 72, various types of information related to imaging may be stored in addition to the OCT image generated from the OCT data. The display unit 75 may display the OCT image generated from the OCT data.

For example, the control unit 70 may drive the drive unit 205 provided in the FPN generation optical system 200 to control a position of the FPN generation member 204.

For example, the control unit 70 may be connected to the wavelength sweep light source 102. For example, the control unit 70 may change a sweep frequency of the wavelength sweep light source 102 between the first sweep frequency H1 and the second sweep frequency H2.

For example, when the sweep frequency is the first sweep frequency H1, a tomographic image of a fundus of the subject eye E is captured. For example, when the sweep frequency is the second sweep frequency H2, a tomographic image of the entire eyeball of the subject eye E is captured. As a method for changing an imaging range in a depth direction according to the sweep frequency, the method described in JP-A-2012-75640 can be used.

For example, a mode in which imaging is performed when the sweep frequency is the first sweep frequency H1 may be set as a first imaging mode, and a mode in which imaging is performed when the sweep frequency is the second sweep frequency 112 may be set as a second imaging mode. In that case, the control unit 70 may also serve as selection means for selecting an imaging mode. For example, the control unit 70 may select the imaging mode based on a signal input by an operator to the control unit 70 via input means (for example, a switch) (not illustrated).

The imaging mode is not limited to the mode in which the imaging range is changed for each sweep frequency. For example, by changing the sweep frequency of the wavelength sweep light source 102, an imaging time and a sensitivity of imaging may be changed. For example, the imaging mode may be a first imaging mode in which imaging is performed with a standard sensitivity and a second imaging mode in which imaging is performed with a higher sensitivity than the first imaging mode. For example, the imaging mode may be a first imaging mode in which imaging is performed in a standard time and a second imaging mode in which imaging is performed in a shorter time than the first imaging mode.

Further, the control unit 70 may control insertion and removal of the shutter 151. Furthermore, the control unit 70 may control insertion and removal of the bandpass filter 301 and the notch filter 302.

In addition, the control unit 70 may be used as an image processor that arithmetically processes a spectral interference signal detected by the detector 120, acquires OCT data, and generates an OCT image.

For example, the control unit 70 may also serve as a computation controller that obtains correction information based on an FPN signal on OCT data (details will be described in [Operation]). In that case, the memory 72 may store an arithmetic processing program for obtaining correction information for correcting a mapping state of a wavenumber component.

Further, for example, the control unit 70 may also serve as a computation controller that calibrates the correction information, based on a calibration interference signal (details will be described in [Operation]). In that case, the memory 72 may store a calibration processing program for calibrating the correction information.

Operation

Figure 2:
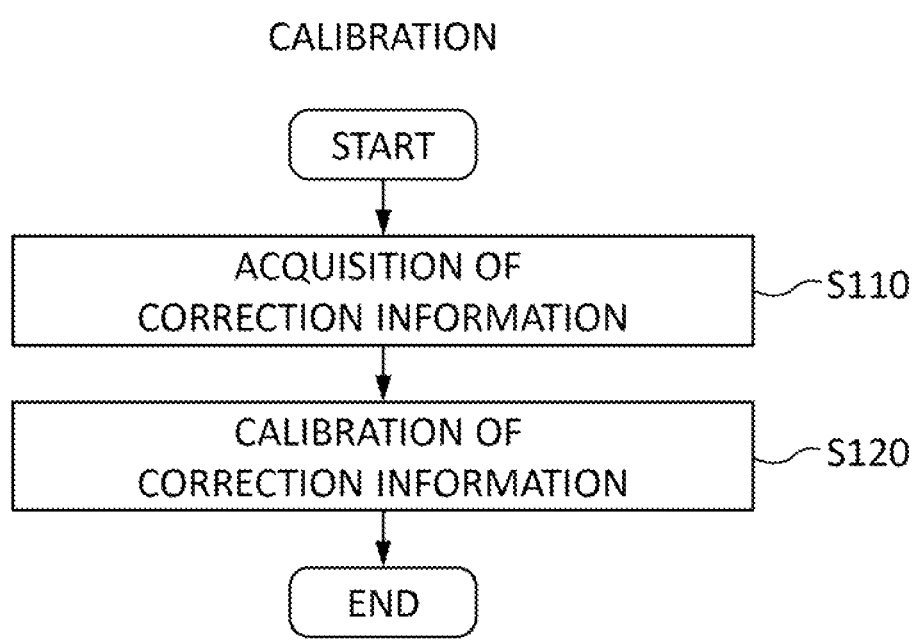
FIG. 2 is a flowchart of control performed by a control unit as calibration.

The OCT apparatus 1 having the above configuration performs calibration so as to correct a mapping state of a wavenumber component and a correspondence deviation. For example, control of the control unit 70 in a case where calibration is performed will be described with reference to FIG. 2. FIG. 2 is a flowchart of the control performed by the control unit 70 in a case where calibration is performed.

In the present embodiment, as calibration, acquisition of correction information by using an FPN (step S110) and calibration of the correction information by using a calibration interference signal (step S120) are performed.

For example, calibration is executed before OCT data of the subject eye E is acquired. In that case, correction information, which will be described below, obtained by the calibration may be held in the memory 72. According to this, since a time for performing calibration at a time of imaging can be reduced, it is possible to acquire the corrected OCT data in a shorter time.

Hereinafter, details of the calibration in the present embodiment will be described.

<S110: Acquisition of Correction Information>

In the present embodiment, the control unit 70 acquires correction information for correcting a mapping state of a wavenumber component, based on an FPN generated by the FPN generation optical system 200. For example, in a case where OCT data of the subject eye E is obtained after calibration, the OCT data in which the mapping state of the wavenumber component is corrected is acquired by performing an arithmetic process by using the correction information.

In the present embodiment, the correction of the mapping state of the wavenumber component includes correction so that a correspondence between a sampling point and a wavenumber of light ($2\pi/\lambda$) becomes linear in OCT data.

Further, in the present embodiment, the correction of the mapping state of the wavenumber component includes correction so that a dispersion component included in the OCT data is removed.

Figure 3A:
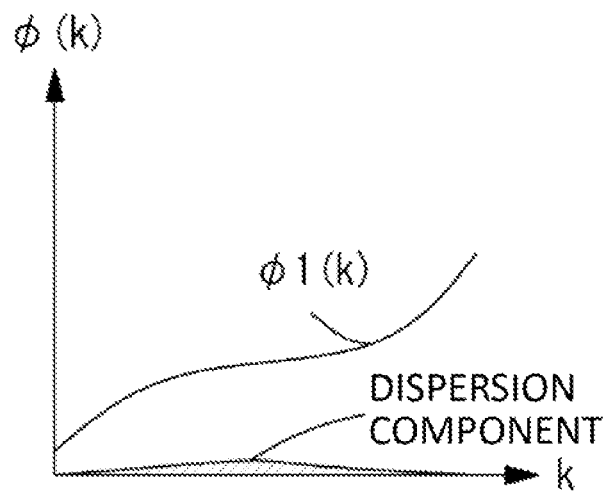
FIGS. 3A and 3B are examples of mapping information of wavenumber components obtained based on an FPN signal.
Figure 3B:
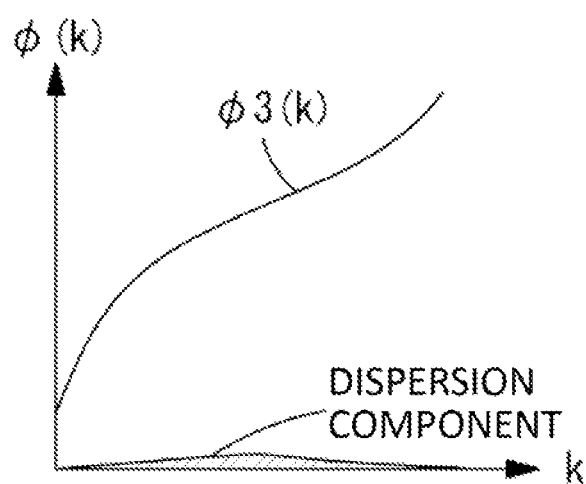
Figure 4:
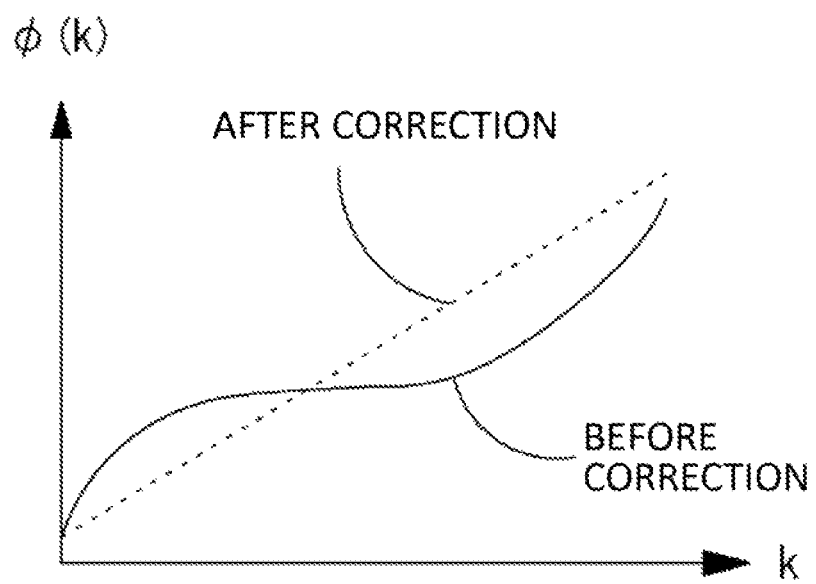
FIG. 4 is a diagram illustrating that a wavenumber mapping state of the wavenumber components is corrected based on correction information.

FIGS. 3A and 3B are examples of mapping information of wavenumber components obtained based on an FPN signal. FIG. 3A is mapping information of a wavenumber component obtained based on a first FPN signal. FIG. 3B is mapping information of a wavenumber component obtained based on a third FPN signal. FIG. 4 is a diagram describing that a wavenumber mapping state of a wavenumber component is corrected based on correction information.

For example, when a sweep frequency of the wavelength sweep light source 102 is changed, a mapping state of a wavenumber component and a dispersion component included in a signal component may be changed.

In the present embodiment, the control unit 70 obtains correction information for each sweep frequency so as to appropriately correct the mapping state of the wavenumber component even in a case where the sweep frequency is changed. For example, the control unit 70 obtains first correction information for correcting a mapping state of a wavenumber component in a case where a sweep frequency is the first sweep frequency Ell, and obtains second correction information for correcting the mapping state of the wavenumber component in a case where the sweep frequency is the second sweep frequency H2.

Figure 5:
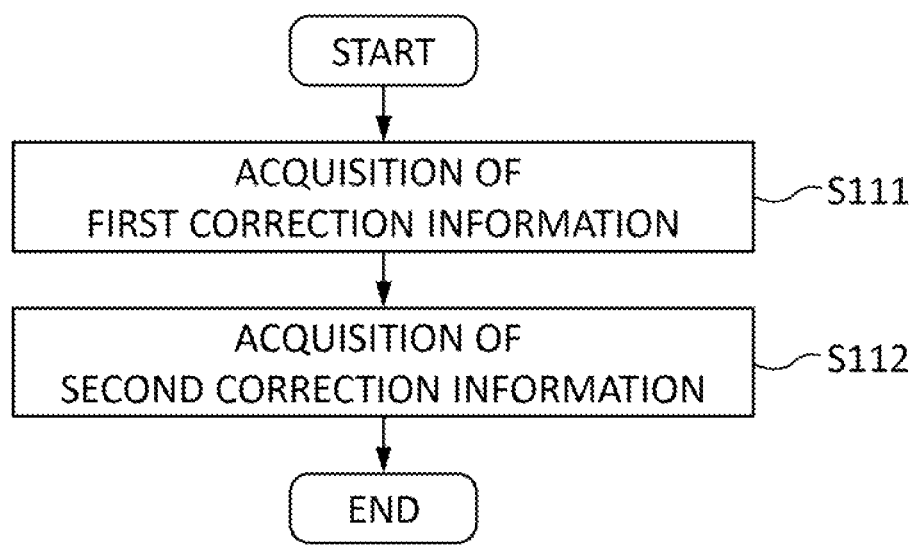
FIG. 5 is a flowchart of control performed by the control unit when the correction information is acquired.

The control performed by the control unit 70 in a case where the first correction information and the second correction information are acquired will be described with reference to the flowchart of FIG. 5. FIG. 5 is a flowchart of control performed by the control unit 70 as acquisition of correction information (step S110).

<S111: Acquisition of First Correction Information>

Figure 6:
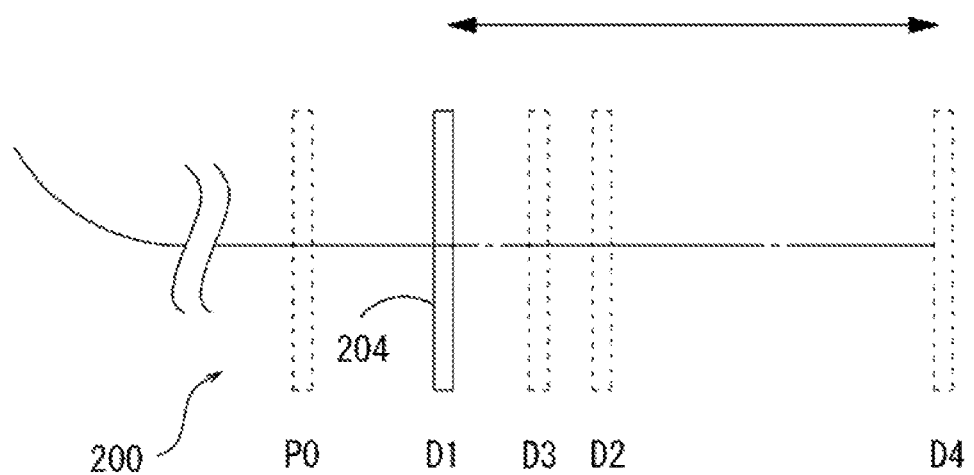
FIG. 6 is a diagram illustrating an example of an FPN generation optical system.
Figure 7A:
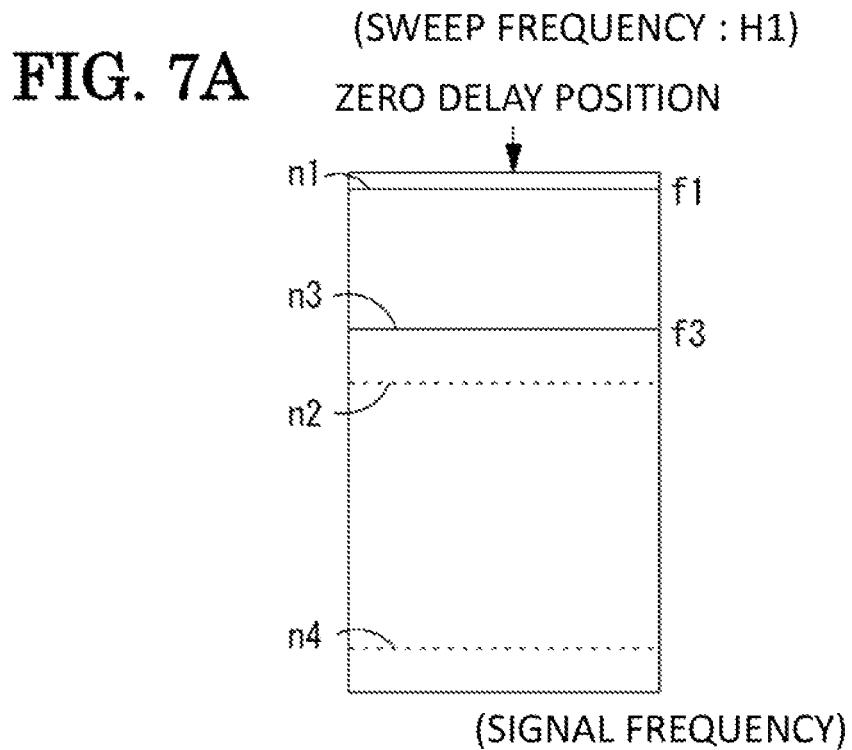
FIGS. 7A and 7B are diagrams illustrating the FPN signal generated by the FPN generation optical system.
Figure 7B:
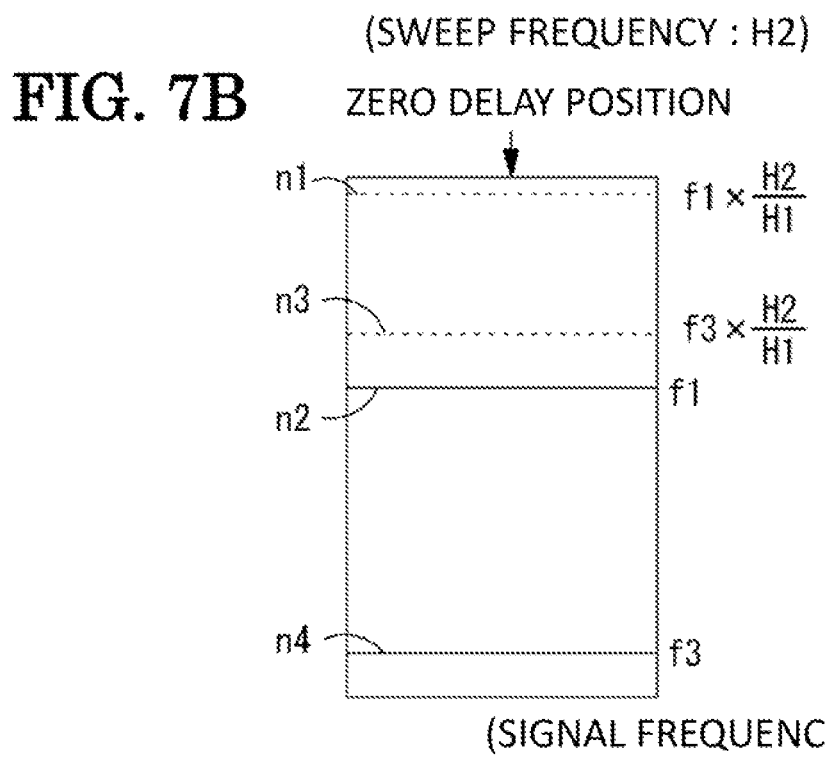

For example, the control unit 70 acquires correction information by using at least two FPNs, among FPNs generated by the FPN generation optical system 200. Further, the control unit 70 acquires correction information for each sweep frequency of the wavelength sweep light source 102. In the present embodiment, in a case where the sweep frequency of the wavelength sweep light source 102 is the first sweep frequency H1, the control unit 70 performs an arithmetic process based on a first FPN signal and a third FPN signal to acquire first correction information. The FPN generation optical system 200 and the generated FPN signal in this case will be described with reference to FIGS. 6, 7A, and 7B. FIG. 6 is a diagram illustrating disposition of the FPN generation member 204 of the FPN generation optical system 200. FIGS. 7A and 7B are diagrams illustrating an FPN signal generated by the FPN generation optical system 200.

In the present embodiment, the drive unit 205 moves the FPN generation member 204 in an optical axis direction to change an optical distance from the origin position P0 to the FPN generation member 204. For example, in a case where the FPN generation member 204 is disposed at a first distance D1, the first FPN signal is generated. In the same manner, in a case where the FPN generation member 204 is disposed at a second distance D2, a second FPN signal is generated. In a case where the FPN generation member 204 is disposed at a third distance D3, the third FPN signal is generated. In a case where the FPN generation member 204 is disposed at a fourth distance D4, a fourth FPN signal is generated.

The first distance D1, the second distance D2, the third distance D3, and the fourth distance D4 are positions that are experimentally determined in advance.

First, the control unit 70 controls the drive unit 205 and moves the position of the FPN generation member 204 so that the distance from the origin position P0 becomes the predetermined first distance D1 (see FIG. 6).

For example, in the present embodiment, a signal frequency of the first FPN signal is set to a first signal frequency f1. It is desirable that the first signal frequency f1 is, for example, a frequency to the extent that the first FPN signal does not enter a zero delay position or the lower frequency when the first FPN signal is Fourier transformed. This is because, in a case where the FPN signal is detected from a spectral interference signal, the lower the frequency of the FPN signal, the less noise the FPN signal can be analyzed with high accuracy.

When the position of the FPN generation member 204 is disposed at the first distance D1, light is emitted from the wavelength sweep light source 102 at the first sweep frequency H1, and the detector 120 detects the spectral interference signal including the first FPN signal.

The control unit 70 analyzes a generated OCT image to obtain $\phi(k)$ in the spectral interference signal at a position corresponding to a first FPN. k indicates a wavenumber, and $\phi(k)$ indicates a change in phase $\phi$ of the spectral interference signal according to the sweep wavelength (wavenumber). For example, wavenumber mapping information is information representing a correspondence between k and $\phi(k)$. $\phi(k)$ may be represented by a function having a horizontal axis: wavenumber k and a vertical axis: phase $\phi$. Polynomial fitting may be performed on $\phi(k)$ in the wavenumber k region in which a signal intensity (amplitude) is large, and $\phi(k)$ in the wavenumber k region in which the signal intensity is small may be obtained by extrapolation or interpolation. For example, $\phi(k)$ may be obtained from Arc Tangent (inverse tangent) of a ratio of a real part RealF and an imaginary part ImagF of a Fourier transform value (intensity value) F at a depth position corresponding to an FPN. Here, in the Arc Tangent process, the inverse tangent of the ratio of the real part and the imaginary part of the Fourier transform value is calculated, and $\phi(k)$ is obtained.

As the method of obtaining $\phi(k)$ from the FPN and the method of obtaining mapping information of wavenumber components from the FPN, the methods described in JP-A-2013-156229 or JP-A-2015-068775 can be used.

For example, in the present embodiment, the control unit 70 processes the first FPN to obtain first wavenumber mapping information $\phi 1(k)$ (see FIG. 3A).

Next, the control unit 70 moves the FPN generation member 204 to the third distance D3 (see FIG. 6).

Here, a signal frequency of the third FPN signal generated by the FPN generation member 204 placed at the third distance D3 is defined as a third signal frequency f3. The third signal frequency f3 is a signal frequency different from the first signal frequency f1. For example, the third FPN with the third signal frequency f3 is generated at a position deeper in a depth direction than a tomographic image of the subject eye E. Therefore, the tomographic image of the subject eye E and the third FPN do not overlap with each other, and the FPN signal can be acquired accurately. The third signal frequency f3 is not limited to this. For example, in a case where return light from the light guide optical system 150 is intercepted by the shutter 151, a tomographic image of the subject eye E does not occur on the OCT image. Therefore, it is not always necessary to generate the FPN at a position deeper in the depth direction than the tomographic image of the subject eye E.

For example, the third FPN may be generated at a position distinguishable from the first FPN when the control unit 70 obtains the mapping information of the wavenumber component. For example, the third FPN is generated at a position separated from the first FPN by 1 mm or more in the depth direction.

When the FPN generation member 204 is disposed at the third distance D3, light is emitted from the wavelength sweep light source 102 at the first sweep frequency H1, and the detector 120 acquires a spectral interference signal including the third FPN signal. After that, the control unit 70 processes the third FPN in the same manner as the first FPN to obtain third wavenumber mapping information $\phi 3(k)$ (see FIG. 3B).

Next, the control unit 70 obtains difference information $\Delta\phi 1\text{-}3(k)$ between the first wavenumber mapping information φ1(k) and the third wavenumber mapping information φ3(k), as first correction information (see FIG. 4). The difference information may be obtained as phase difference information of the wavenumber component. In a case where the difference information Δφ(k) is obtained, phase advance of the third FPN is faster, so that the difference information may be obtained by A φ1-3(k)=φ3(k)−φ1(k). By obtaining the difference information, a dispersion component included in the mapping information of the wavenumber component can be canceled.

In a case where the wavelength sweep light source 102 sweeps a wavelength at the first sweep frequency H1, the control unit 70 corrects the mapping state of the wavenumber component based on the first correction information (see FIG. 4). As the method of correcting the mapping state of the wavenumber component from the difference information of the mapping information of the wavenumber component, the method described in JP-A-2018-124188 can be used.

<S112: Acquisition of Second Correction Information>

As described above, in the present embodiment, the control unit 70 obtains second correction information to correct a mapping state of a wavenumber component in a case where the wavelength sweep light source 102 sweeps a wavelength at the second sweep frequency 112.

Here, if the wavelength is swept at the second sweep frequency H2, a first FPN signal may not be appropriately acquired. The reason for this will be described in detail with reference to FIGS. 8A and 8B. FIGS. 8A and 8B are diagrams describing that a signal frequency at which an FPN signal is detected is changed for each sweep frequency. FIG. 8A illustrates a Fourier transform of the first FPN signal in a case of the first sweep frequency H1. Further, FIG. 8B illustrates a Fourier transform of the first FPN signal in a case of the second sweep frequency H2.

For example, when the sweep frequency is changed, the signal frequency at which an FPN is detected is also changed.

For example, in a case where the sweep frequency is the first sweep frequency H1 (200 kHz for explanation), the first FPN signal is detected as an interference signal with a signal frequency of 100 MHz.

Here, for example, if the sweep frequency is changed to the second sweep frequency H2 (25 kHz for explanation), the sweep frequency becomes 25/200=1/8 times. Therefore, in a case of the second sweep frequency H2, the first FPN signal is detected as an interference signal having a signal frequency of 100 MHz×1/8=12.5 MHz. The numerical values used in this calculation are values used for convenience for explanation, and are not limited thereto.

As in the above example, in a case where the sweep frequency is changed from the first sweep frequency H1 to the second sweep frequency H2 which is lower than the first sweep frequency H1, the signal frequency at which the FPN is detected becomes lower.

For example, the first FPN signal detected at the first signal frequency f1 at the first sweep frequency H1 is detected at a signal frequency obtained by multiplying the first signal frequency f1 by H2/H1 at the second sweep frequency H2 (see FIGS. 7A and 7B). In the same manner, the third FPN signal detected at the third signal frequency f3 at the first sweep frequency H1 is detected at a signal frequency obtained by multiplying a signal frequency corresponding to the third signal frequency f3 by H2/H1 at the second sweep frequency H2.

As described above, in a case where the sweep frequency is the first sweep frequency H1, the lower the first signal frequency f1, the easier the analysis. On the other hand, for example, as the first signal frequency f1 is on the lower peripheral side, an envelope EV1 of a peak of the first FPN signal is generated on the lower frequency side in a case where the sweep frequency is set to the second sweep frequency H2. Therefore, a possibility that the envelope EV1 of the peak of the first FPN signal enters a zero delay region is increased (see FIG. 8B). The zero delay region will be described below.

In the present embodiment, a filter 71 is provided between the detector 120 and the control unit 70. The filter 71 removes an electrical DC component for protecting the control unit 70. For example, the filter 71 removes signals in a region from a zero delay to a predetermined frequency (for example, 10 MHz). In the present embodiment, the region removed by the filter 71 is referred to as the zero delay region.

For example, in the present embodiment, in a case of the second sweep frequency H2, the envelope EV1 of the peak of the first FPN signal may enter the zero delay region and be cut by the filter 71. In this case, it is difficult to obtain appropriate correction information from the first FPN signal.

As described above, in a case of acquiring the second correction information, the first FPN signal may not be appropriately acquired. In the same manner, in a case of acquiring the second correction information, the third FPN signal may not be appropriately acquired.

Therefore, in the present embodiment, in a case where the sweep frequency of the wavelength sweep light source 102 is the second sweep frequency 112, the control unit 70 performs an arithmetic process based on a second FPN signal and a fourth FPN signal to acquire the second correction information.

Figure 9:
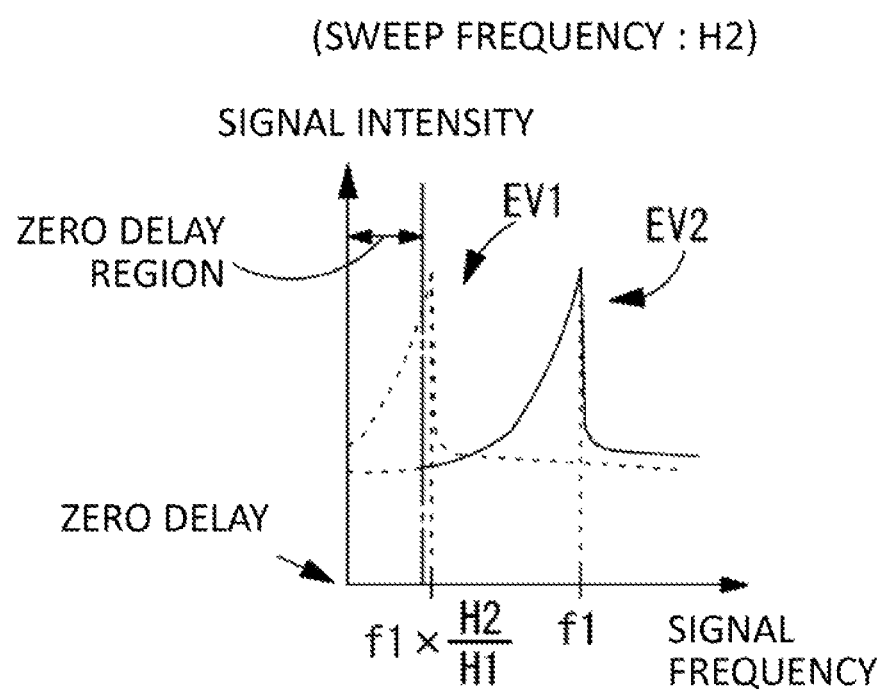
FIG. 9 is a Fourier transform of a second FPN signal in a case where the sweep frequency of a wavelength sweep light source is a second sweep frequency.

For example, the control unit 70 changes a position of the FPN generation member 204 to the second distance D2, and generates the second FPN signal. In the present embodiment, the second FPN signal is a signal frequency that is not cut by the filter 71 in a case where the sweep frequency is set to the second sweep frequency H2. FIG. 9 illustrates a Fourier transform of the second FPN signal in a case where a sweep frequency of the wavelength sweep light source 102 is the second sweep frequency H2.

For example, in a case where the sweep frequency is the second sweep frequency H2, a signal frequency at which the second FPN signal is detected is a signal frequency at which the first FPN signal is detected in a case where the sweep frequency is the first sweep frequency H1 (for example, 100 MHz) (see FIGS. 7A and 7B). The signal frequency at which the second FPN signal is detected is not limited to this, and an envelope EV2 of a peak formed when the second FPN signal is Fourier transformed may exist on the higher frequency side than the zero delay region.

When the position of the FPN generation member 204 is changed to the second distance D2, light is emitted from the wavelength sweep light source 102, and the detector 120 acquires a spectral interference signal including the second FPN signal. After that, the control unit 70 processes the second FPN signal in the same manner as in step S111 to obtain second wavenumber mapping information t 2(k).

Next, the control unit 70 drives the drive unit 205 to move the FPN generation member 204 to the fourth distance D4 so that the fourth FPN is generated. For example, in a case where the sweep frequency is the second sweep frequency H2, a signal frequency at which the fourth FPN signal is detected is a signal frequency at which the third FPN signal is detected in a case where the sweep frequency is the first sweep frequency H1 (see FIGS. 7A and 7B). The signal frequency at which the fourth FPN signal is detected is not limited to this, and an envelope of a peak formed when the fourth FPN signal is Fourier transformed may exist on the higher frequency side than the zero delay region.

After that, the control unit 70 processes the fourth FPN signal in the same manner as in step S111 to obtain fourth wavenumber mapping information $\phi 4(k)$.

Further, the control unit 70 obtains difference information $\Delta\phi 2\text{-}4(k)$ between the second wavenumber mapping information $\phi 2(k)$ and the fourth wavenumber mapping information $\phi 4(k)$, as the second correction information.

In a case where the wavelength sweep light source 102 sweeps a wavelength at the second sweep frequency H2, the control unit 70 corrects a mapping state of a wavenumber component based on the second correction information.

According to the above steps S111 and S112, the first correction information for correcting the mapping state of the wavenumber component in a case where the sweep frequency is the first sweep frequency H1 and the second correction information for correcting the mapping information of the wavenumber component in a case where the sweep frequency is the second sweep frequency H2 are acquired.

When acquiring OCT data, the control unit 70 performs the arithmetic process based on the first correction information or the second correction information, so that regarding the mapping state of the wavenumber component, a nonlinearity of the wavenumber component and a dispersion component can be corrected (see FIG. 4).

In a case of acquiring correction information, the control unit 70 may insert the shutter 151 into the light guide optical system 150. According to this, it is possible to suppress the influence of light derived from the light guide optical system 150 on the correction information, so that the correction information can be appropriately acquired. The light derived from the light guide optical system 150 is, for example, scattered light (return light) from the subject eye E.

<S120: Calibration of Correction Information>

Next, the control unit 70 corrects a correspondence deviation by using the calibration optical system 300. In the present embodiment, the correspondence deviation refers to a deviation in correspondence between a time and a wavenumber of light emitted during a wavelength sweep of the wavelength sweep light source 102, as described above. For example, the correspondence deviation may occur due to environmental factors such as secular variation or temperature.

For example, the correction information acquired in step S110 may be obtained based on an FPN acquired in a state in which this correspondence deviation exists. In this case, in a spectral interference signal acquired by the detector 120, the correction information and a wavelength (or wavenumber) value deviate from each other, so that it is difficult to appropriately perform correction.

For example, in the present embodiment, the control unit 70 calibrates the correction information. For example, when acquiring OCT data of a subject eye in the present embodiment, the control unit 70 performs an arithmetic process by using the calibrated correction information. As a result, the correspondence deviation included in a mapping state of a wavenumber component is corrected. In the present disclosure, the arithmetic process for calibrating the correction information is referred to as a calibration process.

Figure 10:
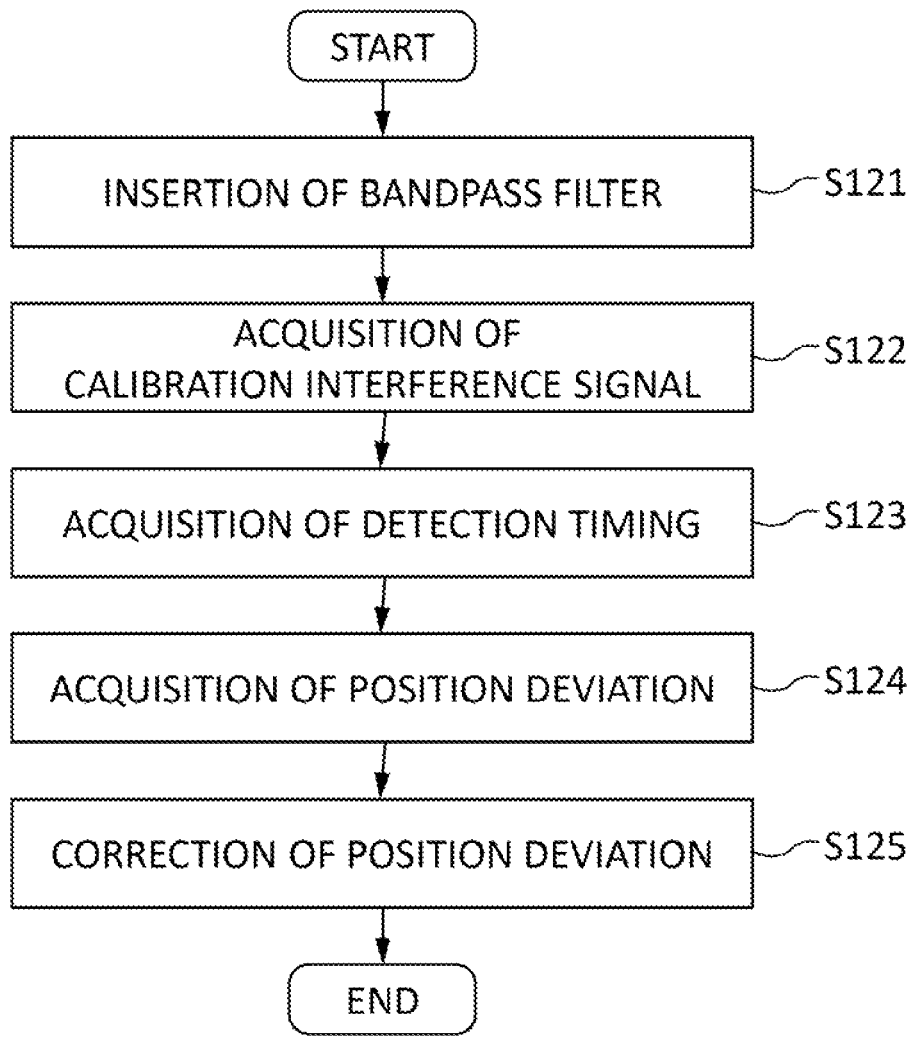
FIG. 10 is a flowchart of control performed by the control unit as calibration of correction information.
Figure 11:
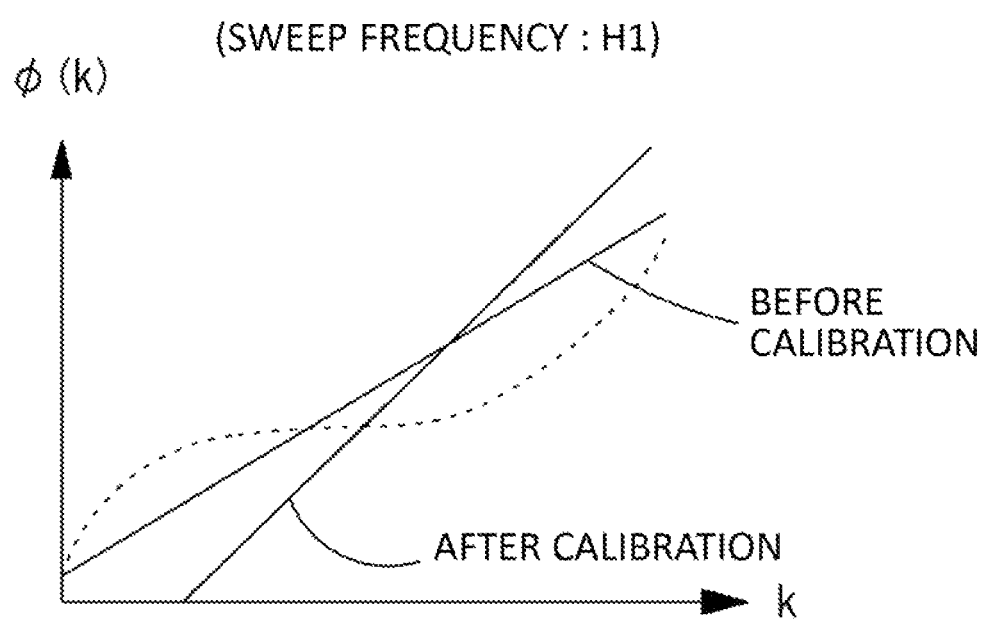
FIG. 11 is a diagram illustrating that a correspondence deviation is corrected by the calibrated correction information.

The control of the control unit 70 for calibrating the correction information will be described with reference to FIGS. 10, 11, 12A, and 12B. FIG. 10 is a flowchart of control performed by the control unit 70 as calibration of correction information (step S120). FIG. 11 is a diagram describing that a correspondence deviation in mapping state of a wavenumber component is corrected by the calibrated correction information. FIG. 11 illustrates mapping information of a wavenumber component in a case where an arithmetic process is performed by using the correction information before calibration and mapping information of the wavenumber component in a case where the arithmetic process is performed by using the correction information after calibration. FIGS. 12A and 12B are diagrams illustrating that a correspondence deviation included in a wavenumber mapping state is corrected by performing calibration.

For example, in the present embodiment, due to the correspondence deviation, there is a change in graph slope between a graph of the mapping information of the wavenumber component based on the correction information before calibration and a graph of the mapping information of the wavenumber component based on the correction information after calibration, as illustrated in FIG. 12A. For example, in the present embodiment, due to the correspondence deviation, there is a graph shift (parallel translation) between a graph of the mapping information of the wavenumber component based on the correction information before calibration and a graph of the mapping information of the wavenumber component based on the correction information after calibration, as illustrated in FIG. 12B.

<S121: Insertion of Bandpass Filter>

First, the control unit 70 inserts the bandpass filter 301 and the notch filter 302 into an optical axis of the calibration optical system 300 (also used as the FPN generation optical system 200).

In the present embodiment, the bandpass filter 301 and the notch filter 302 selectively extract light having a predetermined first wavelength, and light having a second wavelength different from the first wavelength, included in a sweep range of the wavelength sweep light source 102.

<S122: Acquisition of Calibration Interference Signal>

When the wavelength sweep light source 102 performs a sweep at the first sweep frequency H1 in a state in which the bandpass filter 301 and the notch filter 302 are inserted in the calibration optical system 300, the swept light passes through the calibration optical system 300, and the light having the first wavelength and the light having the second wavelength are extracted.

The extracted light is combined with reference light by the coupler 350, and detected by the detector 120 as a spectral interference signal. In the present embodiment, the spectral interference signal due to the extracted light and the reference light is referred to as a calibration interference signal. For example, a spectral interference signal by the light extracted in a case where the sweep frequency of the wavelength sweep light source is swept at the first sweep frequency H1 and the reference light is referred to as a first calibration interference signal. For example, the first calibration interference signal includes a calibration interference signal G1 by the light having the first wavelength and the reference light and a calibration interference signal G2 by the light having the second wavelength and the reference light.

In the present embodiment, the bandpass filter 301 and the notch filter 302 are retracted with respect to an optical axis of the FPN generation optical system 200, except in a case where the calibration interference signal is acquired.

Figure 13:
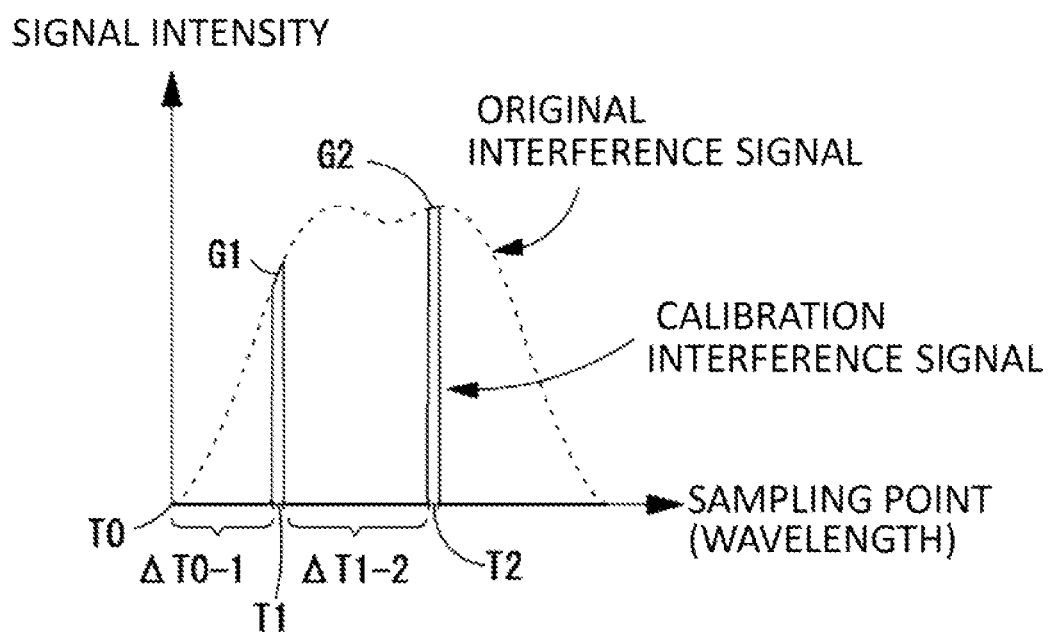
FIG. 13 is a diagram illustrating a spectral interference signal acquired by a calibration optical system.

The calibration interference signal will be described with reference to FIG. 13. FIG. 13 is a diagram illustrating an example of a first calibration interference signal.

As the first calibration interference signal, the calibration interference signal G1 by the light having the first wavelength and the reference light is detected, at a sampling point (first detection timing) T1 corresponding to a timing when the wavelength sweep light source 102 emits the light having the first wavelength.

For example, it is technically difficult to extract only the light having the first wavelength, by the bandpass filter 301 and the notch filter 302. Therefore, the calibration interference signal G1 includes not only a component of an interference signal by the light having the first wavelength and the reference light, but also a component of the interference signal by light other than the first wavelength and the reference light.

For example, in the present embodiment, light having a wavelength closer to the first wavelength is more likely to pass through the bandpass filter 301 and the notch filter 302. Therefore, for example, the calibration interference signal G1 is a mountain-shaped waveform interference signal having an interference signal by the light having the first wavelength and the reference light as a peak.

In the same manner, at a sampling point (second detection timing) T2 corresponding to a timing when the wavelength sweep light source 102 emits the light having the second wavelength, the calibration interference signal G2 by the light having the second wavelength and the reference light is detected.

In a case of acquiring the first calibration interference signal, for example, it is assumed that the FPN generation member 204 of the FPN generation optical system 200 is disposed at the first distance D1. In the present embodiment, an optical path length difference between an optical path length of the calibration optical system 300 and an optical path length of the reference optical system 110 in a case where the FPN generation member 204 is disposed at the first distance D1 is a first optical path length difference. Further, the first distance D1 is an example of a position of the FPN generation member 204, and is not limited to this.

The control unit 70 acquires the first calibration interference signal, and then acquires a second calibration interference signal. For example, the control unit 70 drives the drive unit 205 to move the FPN generation member 204 from the first distance D1 to another distance. For example, the control unit 70 moves the FPN generation member 204 to the second distance D2.

For example, in the present embodiment, an optical path length difference between an optical path length of the calibration optical system 300 and an optical path length of the reference optical system 110 in a case where the FPN generation member 204 is at the second distance D2 is a second optical path length difference. The second distance D2 is an example of a distance at which the FPN generation member 204 is disposed, and is not limited thereto.

For example, in the present embodiment, the drive unit 205 also serves as changing means for changing an optical path length difference between a reference optical path and a measurement optical path.

When the position of the FPN generation member 204 is moved to the second distance D2, the wavelength sweep light source 102 performs a sweep at the first sweep frequency H1. As a result, the detector 120 detects the second calibration interference signal as well as the first calibration interference signal.

Here, in a case of detecting the second calibration interference signal, a wavelength is swept at the same first sweep frequency H1 as in a case of obtaining the first calibration interference signal, so that a timing at which the light having the first wavelength is emitted is also the same. Therefore, on the second calibration interference signal, the calibration interference signal G1 having a waveform different from that of the first calibration interference signal is generated at the same first detection timing T1 as the first calibration interference signal. In the same manner, on the second calibration interference signal, the calibration interference signal G2 having a waveform different from that of the first calibration interference signal is generated at the same detection timing as the first calibration interference signal.

In the present embodiment, the control unit 70 retracts the bandpass filter 301 and the notch filter 302 from the calibration optical system 300 in a case where the acquisition of the calibration interference signal is completed.

<S123: Acquisition of Detection Timing>

Figure 14:
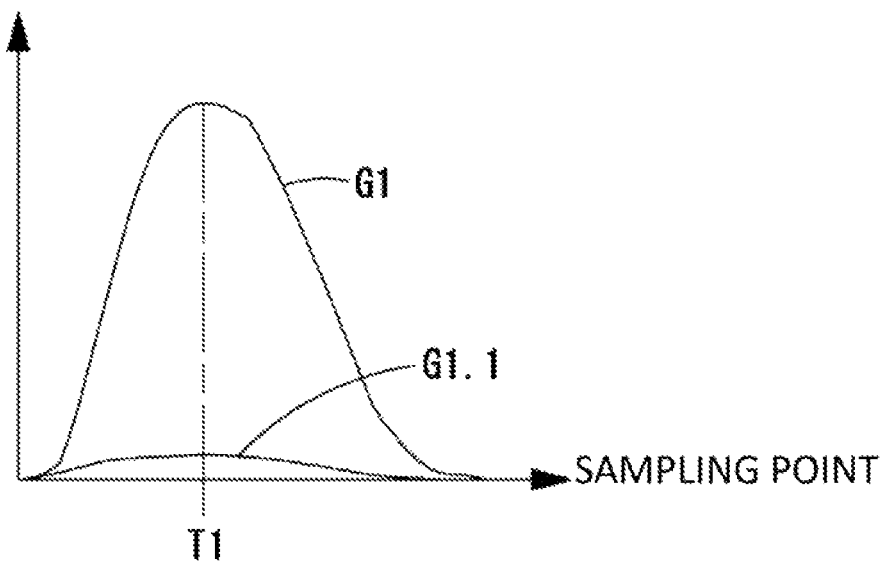
FIG. 14 is a diagram illustrating a calibration interference signal acquired by the calibration optical system.

A method of acquiring a detection timing will be described with reference to FIG. 14. FIG. 14 is a diagram illustrating a waveform of the calibration interference signal G1.

In the present embodiment, the wavelength sweep light source 102 outputs a sweep start signal to the control unit 70 at a timing when a sweep is started. For example, the control unit 70 associates a sampling point of the detector 120 at a timing when the sweep start signal is input from the wavelength sweep light source 102, as a sampling point T0 of a sweep start.

In the present embodiment, for example, the first detection timing T1 and the second detection timing T2 are obtained with reference to the sampling point T0 of the sweep start.

For example, the control unit 70 obtains the sampling point 3 (first detection timing) T1 at which the calibration interference signal G1 is detected based on the first calibration interference signal and the second calibration interference signal. For example, the first detection timing T1 is a sampling point at which a peak of the calibration interference signal G1 exists. For example, the first detection timing T1 is a sampling point at which an interference signal by the light having the first wavelength and the reference light exists.

Here, a signal intensity of the calibration interference signal G1 may be low, depending on the optical path length difference between the reference optical path and the measurement optical path. For example, the calibration interference signal G1 in this case is referred to as the calibration interference signal G1.1 (see FIG. 14). For example, in a case where the signal intensity of the spectral interference signal between the light of the first wavelength and the reference light is low, it may be difficult to detect the peak. In this case, since the peak cannot be detected appropriately, the control unit 70 may not be able to accurately determine the first detection timing T1.

Therefore, in the present embodiment, the control unit 70 processes a plurality of calibration interference signals to increase the signal intensity of the spectral interference signal by the light of the first wavelength and the reference light.

For example, in the present embodiment, absolute values are taken for the first calibration interference signal and the second calibration interference signal, and then averaged. According to this, the signal intensity of the calibration interference signal G1 is cumulatively added. Therefore, the control unit 70 can detect the peak with high accuracy. Therefore, the control unit 70 can accurately acquire the first detection timing T1.

The calibration interference signal used in the calibration process is not limited to the first calibration interference signal and the second calibration interference signal. For example, as the number of calibration interference signals used in the calibration process is increased, the signal intensity of the spectral interference signal by the light of the first wavelength and the reference light can be increased, so that the peak can be detected more easily, and the first detection timing T1 can be obtained with high accuracy.

For example, the method of obtaining the first detection timing T1 is not limited to this. For example, a sampling point when the signal intensity of the interference signal is increased by a predetermined value or more may be set as the first detection timing T1. That is, a sampling point at which the peak rises in the first calibration interference signal may be set as the first detection timing T1. The sampling point may be a sampling point when the signal intensity of the interference signal is decreased by a predetermined value or more. That is, a sampling point at which the peak falls in the calibration interference signal may be set as the first detection timing T1.

Further, in the same manner as the first detection timing T1, the control unit 70 detects the sampling point (second detection timing) T2 at which the calibration interference signal G2 is detected.

<S124: Acquisition of Correspondence Deviation>

The control unit 70 detects a correspondence deviation and obtains the number of sampling points $\Delta T1\text{-}2$ included between the first detection timing T1 and the second detection timing T2 (see FIG. 13).

For example, the control unit 70 obtains a change amount between the value of $\Delta T1\text{-}2$ and a value obtained in advance. For example, the value obtained in advance is a value of $\Delta T1\text{-}2$ obtained when the OCT apparatus 1 is shipped from a factory. The value obtained in advance is not limited to this example, and may be any value of $\Delta T1\text{-}2$ acquired before this calibration.

For example, in a case where the value of $\Delta T1\text{-}2$ is decreased, a time since light having a first wavelength is emitted until light having a second wavelength is emitted is shortened. Therefore, it is considered that a sweep frequency of the wavelength sweep light source 102 is higher than an expected sweep frequency. In a case where the value of $\Delta T1\text{-}2$ is increased, it is considered that the sweep frequency of the wavelength sweep light source 102 is decreased from the expected sweep frequency.

For example, the control unit 70 can correct a deviation in sweep frequency of the wavelength sweep light source 102 by correcting the value of $\Delta T1\text{-}2$. Describing with reference to the drawing, a slope of a graph of a mapping state of a wavenumber component is corrected (see FIG. 12A).

Further, for example, the control unit 70 completes the correction for the sweep frequency, and then obtains a change amount between the value obtained in advance and the value of the number of sampling points $\Delta T0\text{-}1$ from the sampling point T0 at which a sweep is started to the sampling point T1. According to this, after the sweep frequency is corrected, a difference in timing at which light having a predetermined wavenumber is detected can be obtained. Therefore, it is possible to obtain a change in wavelength (wavenumber) at which the wavelength sweep light source 102 starts the sweep.

For example, in a case where the value of $\Delta T0\text{-}1$ is decreased in a state in which a sweep speed is corrected, it is considered that a wavelength at a time of the wavelength sweep start is increasing. For example, in a case where the value of $\Delta T0\text{-}1$ is increased in a state in which the sweep speed is corrected, it is considered that the wavelength (wavenumber) at a time of the wavelength sweep start is decreasing.

For example, the control unit 70 can correct the change amount in $\Delta T0\text{-}1$ to correct a wavelength deviation when the wavelength sweep light source 102 starts the sweep. Describing with reference to the drawing, a shift (parallel translation) of a graph of a mapping state of a wavenumber component is corrected (see FIG. 12I). Not limited to $\Delta T0\text{-}1$, even if the arithmetic operation is performed by using the number of sampling points $\Delta T0\text{-}2$ between the sampling points T0 and the sampling point T2, it is possible to obtain a change in wavelength (wavenumber) at which the wavelength sweep light source 102 starts a sweep, in the same manner.

<S125: Correction of Correspondence Deviation>

The control unit 70 corrects first correction information so that the change amount between the value of $\Delta T1\text{-}2$ and the value obtained in advance is corrected. According to this, the slope of the graph of the mapping state of the wavenumber component is corrected (see FIG. 12A).

Further, the control unit 70 corrects the first correction information so that the change amount between the value of $\Delta T0\text{-}1$ and the value obtained in advance is corrected. According to this, the shift (parallel translation) of the graph of the mapping state of the wavenumber component is corrected.

As a result, in the imaging (S200) which will be described below, the mapping state of the wavenumber component corrected for a correspondence deviation can be acquired (see FIG. 11).

Further, the control unit 70 also corrects the correspondence deviation by replacing the first sweep frequency H1 with the second sweep frequency H2, and executing steps S121 to S125 for second correction information.

As described above, in step S120, the correspondence deviation is corrected for the mapping state of the wavenumber component (see FIG. 11).

Further, since the control unit 70 can acquire a change over time of the wavelength sweep of the wavelength sweep light source 102 by directly analyzing a spectral interference signal without using an OCT image or the like, the deviation can be corrected with high accuracy.

As described above, in the present embodiment, the control unit 70 performs calibration by executing steps S110 and S120. As a result, calibrated correction information is acquired for each sweep frequency. The control unit 70 acquires OCT data of the subject eye by performing the arithmetic process using the calibrated correction information.

For example, the control unit 70 images the subject eye E after retracting the shutter 151 with respect to the optical axis. For example, as described in [Configuration], an imaging range is changed for each sweep frequency of the wavelength sweep light source 102. For example, when light is emitted from the wavelength sweep light source 102, the detector 120 detects a spectral interference signal between reference light and return light from the subject eye E.

For example, the first correction information is used for the arithmetic process on a spectral interference signal obtained in a case where the sweep frequency of the wavelength sweep light source 102 is the first sweep frequency H1. Further, the second correction information is used for the arithmetic process on a spectral interference signal obtained in a case where the sweep frequency of the wavelength sweep light source 102 is the second sweep frequency H2.

Specifically, for example, in a case where the sweep frequency of the wavelength sweep light source 102 is the first sweep frequency H1, the control unit 70 acquires OCT data based on the first correction information obtained in step S110 and calibrated in step S120. Further, in a case where the sweep frequency of the wavelength sweep light source 102 is the second sweep frequency H2, the control unit 70 acquires OCT data based on the second correction information obtained in step S110 and calibrated in step S120.

As a result, the mapping state of the wavenumber component can be appropriately corrected according to the sweep frequency of the wavelength sweep light source 102, so that the OCT data can be appropriately acquired.

As a method of applying the correction information to the arithmetic process on the spectral interference signal and acquiring the OCT data, the method described in JP-A-2018-124188 can be used.

Modification Example

For example, in the present embodiment, the case where the bandpass filter 301 and the notch filter 302 are provided in the FPN generation optical system 200 is described, but for example, the bandpass filter 301 and the notch filter 302 may be provided in the light guide optical system 150. In this case, the calibration optical system 300 is also used as the light guide optical system 150. Further, in a case where a calibration interference signal is obtained with this configuration, the detector 120 detects an interference signal derived from light derived from the calibration optical system 300 (light guide optical system 150), light of the FPN generation optical system 200, and reference light. Therefore, the control unit 70 can acquire a first calibration interference signal and a second calibration interference signal by changing a position of the FPN generation member 204 of the FPN generation optical system 200.

For example, in the present embodiment, the first calibration interference signal and the second calibration interference signal are used to correct the correspondence deviation in step S120, but the interference signal to be used to correct the correspondence deviation may be only the first calibration interference signal. According to this, a time required to correct the correspondence deviation is shortened.

Further, in addition to the first calibration interference signal and the second calibration interference signal, a calibration interference signal may be further used to correct the correspondence deviation. In that case, for example, in step S122, the control unit 70 drives the drive unit 205 to change the position of the FPN generation member 204, and then causes the wavelength sweep light source 102 to sweep a wavelength, so that the calibration interference signal is acquired. Further, by using more calibration interference signals, a peak position can be obtained more accurately in step S124, so that the correspondence deviation can be corrected with high accuracy.

For example, in the present embodiment, the correction information is calibrated based on the calibration interference signal to correct the correspondence deviation. For example, the correspondence deviation may be corrected by calibrating the OCT data of the subject eye E. In that case, for example, the control unit 70 performs the same process as the calibration process performed on the correction information in step S125. The process may be performed on the OCT data of the subject eye E. Further, in that case, calibration may be performed between the acquisition of the OCT data of the subject eye E and the generation of the OCT image.

For example, in the present embodiment, a case where the position of the FPN generation member 204 is changed by driving the drive unit 205 in order to generate an FPN at a different position is described, but a method of generating the FPN at the different position is not limited to this.

Figure 15:
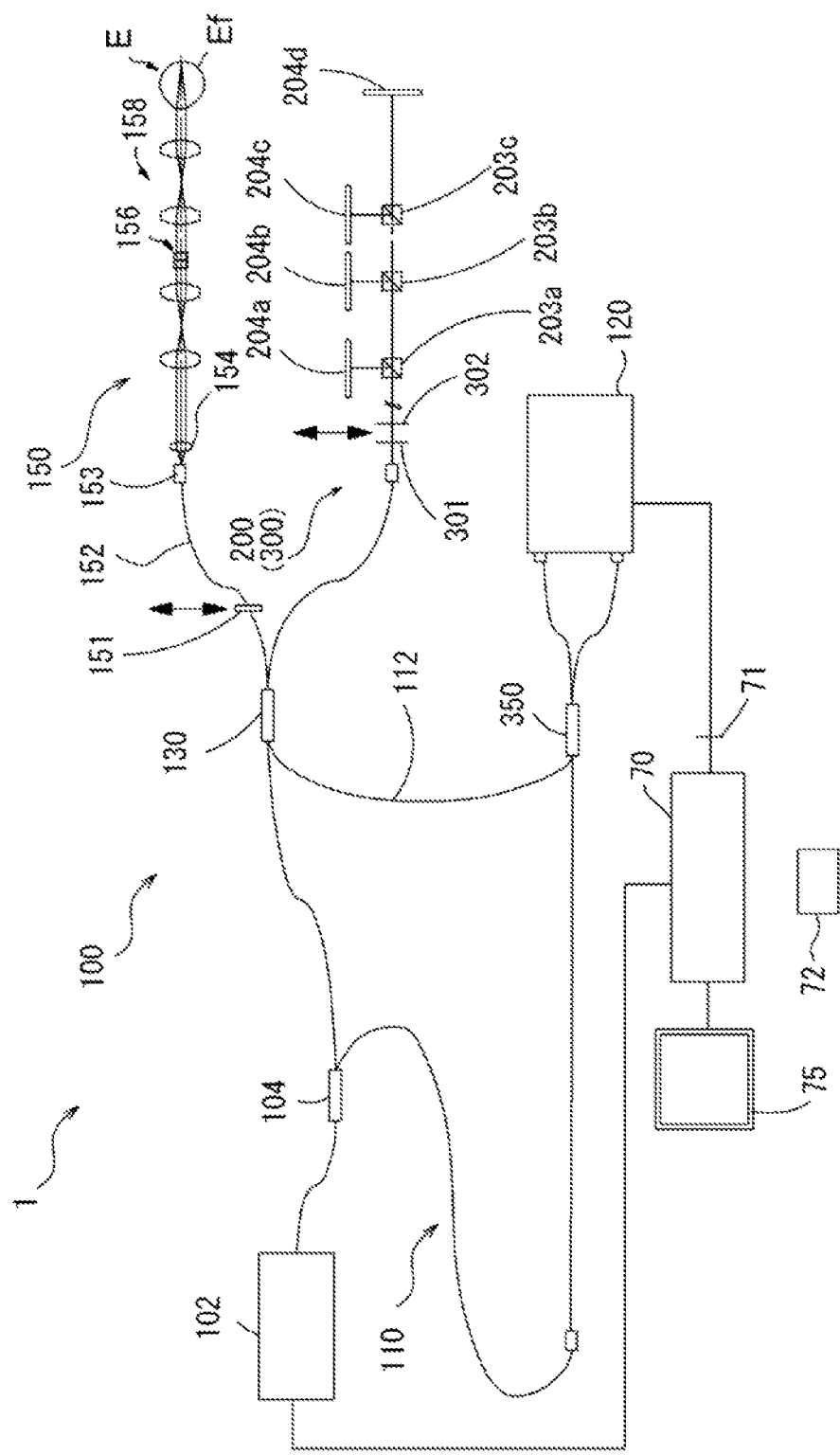
FIG. 15 is a diagram illustrating an example of a modification example of the FPN generation optical system.

For example, as illustrated in FIG. 15, the FPN generation optical system 200 may be provided with a plurality of FPN generation members to generate FPNs at different positions. For example, in the present embodiment, in a case where four FPNs are generated, an FPN generation member 204a may be disposed at a position corresponding to the first distance D1, an FPN generation member 204b may be disposed at a position corresponding to the second distance D2, an FPN generation member 204c may be disposed at a position corresponding to the third distance D3, and an FPN generation member 204d may be disposed at a position corresponding to the fourth distance D4. Further, in this case, optical path dividing members (for example, beam splitters) 203a, 203b, and 203c may be provided in order to guide light to each of the FPN generation members.

Figure 16:
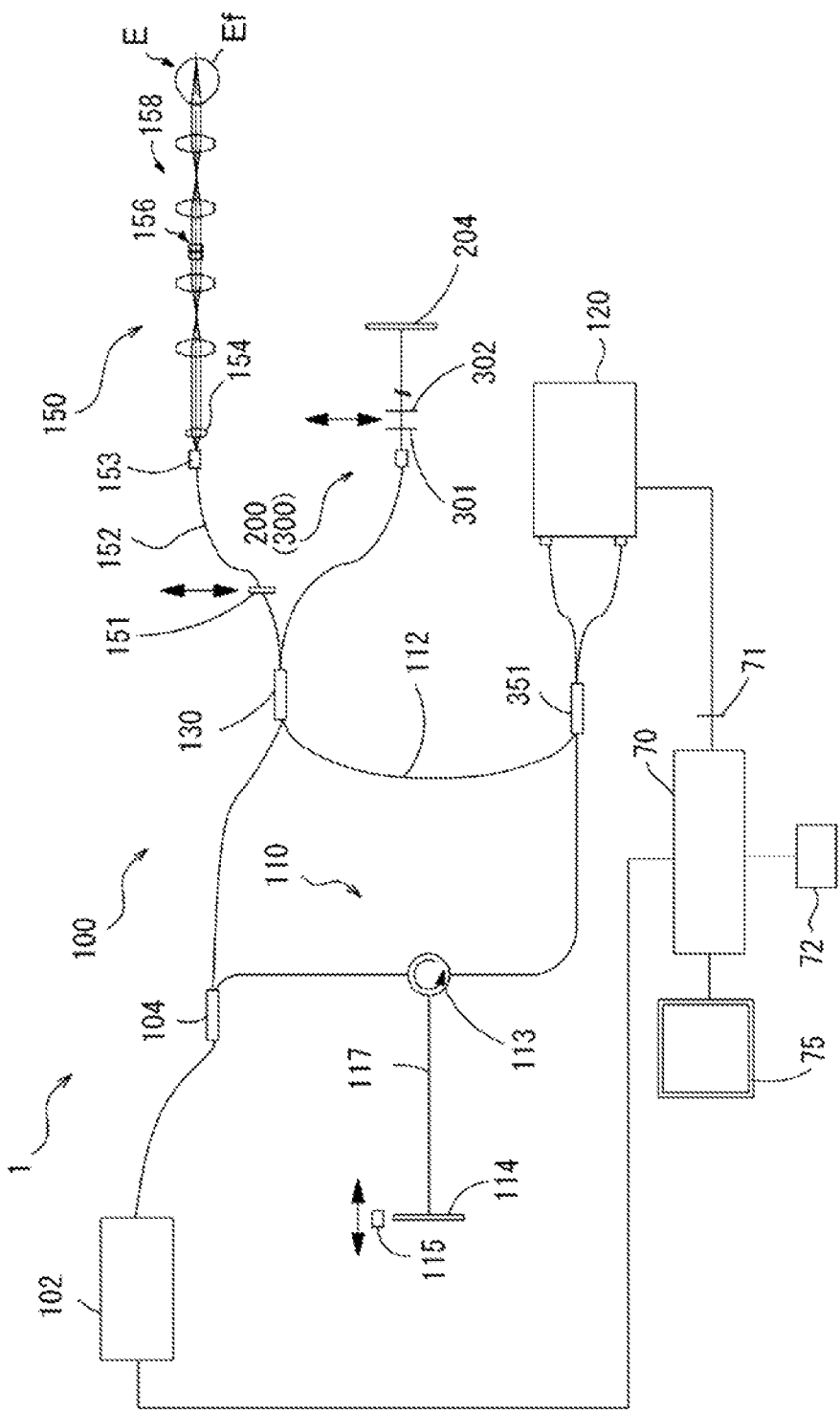
FIG. 16 is a diagram illustrating an example of the modification example of the FPN generation optical system and a reference optical system.

In addition, for example, the position at which the FPN is generated may be changed by changing an optical path length of the reference optical system 110. FIG. 16 is an OCT optical system in a case where a reference mirror 114 is used for the reference optical system 110. In this case, light emitted from the wavelength sweep light source 102 is divided into a measurement optical path and a reference optical path by the coupler (splitter) 104. The light incident on the reference optical system 110 is guided to an optical fiber 117 by a circulator 113, reflected by the reference mirror 114, and incident on a coupler 351. Further, the light incident on the measurement optical path enters the coupler 351 through the light guide optical system 150 (and the FPN generation optical system 200) and the optical fiber 112. The light derived from the reference optical path and the light derived from the measurement optical path are combined by the coupler 351 and interference is detected by the detector 120.

For example, the drive unit 115 moves the reference mirror 114 in an optical axis direction, and the optical path length of the reference optical system 110 is changed. As a result, an optical path length difference between an optical path length of the reference optical system and an optical path length of the FPN generation optical system 200 is changed, and the position at which an FPN is generated is changed. The drive unit 115 may have the same configuration as the drive unit 205 described above.

For example, in this case, the origin position P0 is a position of the reference mirror such that the FPN occurs at a position of a zero delay of an OCT image.

Further, for example, the drive unit 115 may change an optical distance from the origin position P0 to the reference mirror 114 between the first distance D1 at which the first FPN signal is generated, the second distance D2 at which the second FPN signal is generated, the third distance D3 at which the third FPN signal is generated, and the fourth distance D4 at which the fourth FPN signal is generated. According to this, an optical path length of the reference light is changed.

A method of changing the optical path length of the reference optical path is not limited to this. For example, a plurality of optical fibers having different lengths may be provided as reference optical paths, and the FPN generated may be changed depending on the length of the passing optical fiber.

In the present embodiment, the case where the first correction information corresponding to the first sweep frequency H1 and the second correction information corresponding to the second sweep frequency are acquired in step S110 is described, but the first correction information and the second correction information may not necessarily be obtained at the same calibration time, for example.

Further, for example, the first correction information may be acquired in a case where a first imaging mode in which imaging is performed at a first sweep frequency is performed, and the second correction information may be acquired in a case where a second imaging mode in which imaging is performed at a second sweep frequency is performed.

In addition, in the present embodiment, as a calibration, the case where the acquisition of the correction information for each sweep frequency (step S110) and the calibration of the correction information (step S120) are performed as a series is described, but the acquisition of the correction information for each sweep frequency and the calibration of the correction information may not necessarily be performed at the same calibration time. For example, the correction information may be acquired as calibration, and the correction information may not be calibrated. In the same manner, the correction information is calibrated as calibration, and the correction information may not be acquired. In this case, the control unit 70 may calibrate correction information acquired before the calibration is performed (for example, correction information acquired at a time of shipment from the factory) as calibration of the correction information.

Further, for example, in a case where the OCT apparatus 1 has a configuration in which correction information for each sweep frequency is acquired and calibration is not performed on the correction information, the calibration optical system 300 (bandpass filter 301 and notch filter 302) may be omitted.

In a case of acquiring correction information, the control unit 70 may insert the shutter 151 into the light guide optical system 150. According to this, it is possible to suppress the influence of light derived from the light guide optical system 150 on the correction information, so that the correction information can be appropriately acquired. The light derived from the light guide optical system 150 is, for example, scattered light (return light) from the subject eye E.

Further, in the present embodiment, in a case where the correction information is acquired, the bandpass filter 301 and the notch filter 302 are retracted with respect to an optical axis of the FPN generation optical system 200. As a result, the FPN signal can be acquired without being affected by the bandpass filter 301 and the notch filter 302, so that the correction information can be acquired.

An intensity of light emitted from the wavelength sweep light source 102 is changed based on a sweep frequency.

Figure 17:
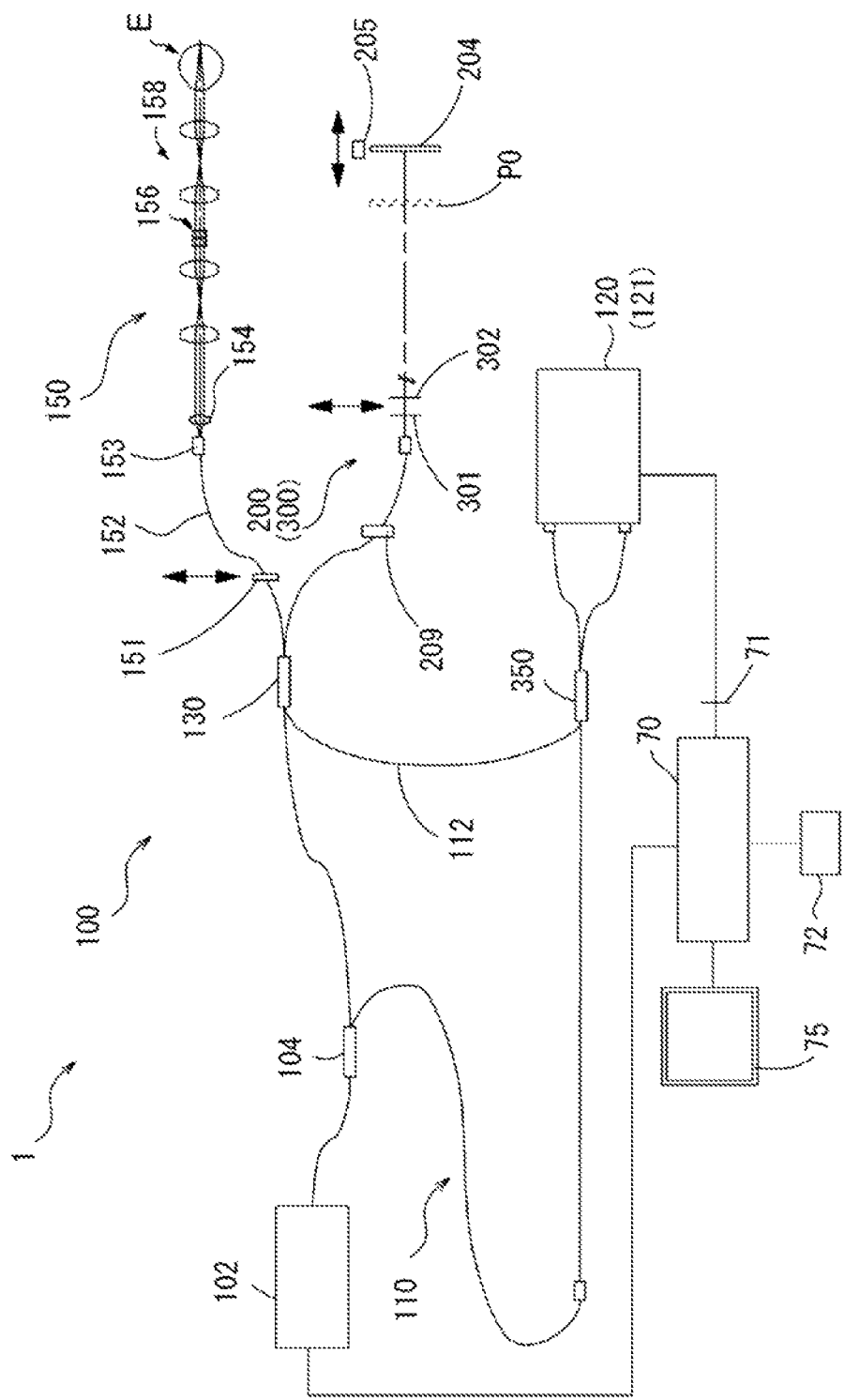
FIG. 17 is a diagram illustrating an example of another modification example of the FPN generation optical system.

For example, as illustrated in FIG. 17, the FPN generation optical system 200 may be provided with a light intensity regulator 209. The light intensity regulator 209 adjusts an intensity of light derived from the FPN generation optical system 200 so as to be included in a predetermined range. For example, the light intensity regulator 209 adjusts the intensity of the light so that an interference signal (that is, an FPN signal) by the light derived from the FPN generation optical system 200 is included in a signal intensity range (dynamic range) in which the detector 120 can detect the signal.

According to this, even if the intensity of the light emitted from the wavelength sweep light source 102 is changed in a case where the sweep frequency is changed, the detector 120 can appropriately acquire the FPN signal.

For example, the light intensity regulator 209 includes a lens and a drive unit that drives the lens in an optical axis direction. For example, the light intensity regulator 209 may be configured with a filter for attenuating light and an insertion and removal unit for inserting and removing the filter with respect to an optical axis. Further, for example, the light intensity regulator may be an attenuator.

For example, the operation of the light intensity regulator 209 is predetermined for each sweep frequency. Further, the operation of the light intensity regulator 209 may be controlled based on a signal intensity of the signal detected by the detector 120.

In the present embodiment, the case where an interference signal including the calibration interference signal G1 and the calibration interference signal G2 is acquired as a first calibration interference signal by combining the bandpass filter 301 and the notch filter 302 is described.

For example, instead of the bandpass filter 301 and the notch filter 302, the calibration optical system 300 may include a first bandpass filter for acquiring the calibration interference signal G1 and a second bandpass filter for acquiring the calibration interference signal G2. The first bandpass filter selectively passes light having the first wavelength. The second bandpass filter selectively passes light having the second wavelength.

In this case, a wavelength is swept in a state where any of the first bandpass filter and the second bandpass filter is selectively inserted with respect to the optical axis, and a calibration interference signal is acquired.

For example, when the wavelength is swept in a state in which the first bandpass filter is inserted with respect to the optical axis and the second bandpass filter is removed from the optical axis, an interference signal A with which the calibration interference signal G1 is generated is acquired, at the first detection timing T1.

For example, when the wavelength is swept in a state in which the second bandpass filter is inserted with respect to the optical axis and the first bandpass filter is removed from the optical axis, an interference signal B with which the calibration interference signal G2 is generated is acquired, at the second detection timing T2.

For example, the control unit 70 may acquire the first calibration interference signal by superimposing the respectively acquired interference signal A and interference signal B.

Of course, the second calibration interference signal can be obtained in the same manner.

What is claimed is:

1. An OCT apparatus comprising:
    a wavelength sweep light source configured to change a sweep frequency between a first sweep frequency and a second sweep frequency smaller than the first sweep frequency;
    an OCT optical system including:
        a light splitter that divides light from the wavelength sweep light source into measurement light and reference light; and
        a first detector that detects a spectral interference signal between the measurement light guided to tissue of a subject eye and the reference light;
    an image processor that performs an arithmetic process on the spectral interference signal to acquire OCT data of the subject eye;
    an FPN generation optical system including at least one optical member that generates a first FPN and a second FPN generated at a position separated from a zero delay position with respect to the first FPN;

a second detector that detects FPNs including the first FPN and the second FPN; and a computation controller configured to:
acquire first correction information based on at least the first FPN detected in a case where the sweep frequency is the first sweep frequency, and acquire second correction information based on at least the second FPN detected in a case where the sweep frequency is the second sweep frequency, the first correction information and the second correction information being information for correcting a mapping state of a wavenumber component; and apply the first correction information to the arithmetic process on the spectral interference signal obtained in the case of the first sweep frequency, and apply the second correction information to the arithmetic process on the spectral interference signal obtained in the case of the second sweep frequency.

2. The OCT apparatus according to claim 1, further comprising:
a drive unit configured to change a distance between the optical member and a zero delay position on the OCT optical system,
wherein the FPN generation optical system generates the first FPN in a case where the distance is a first distance, and generates the second FPN in a case where the distance is a second distance different from the first distance.

3. The OCT apparatus according to claim 1,
wherein the FPN generation optical system has a first optical member and a second optical member, as the optical members, that are arranged of which distances from a zero delay position on the OCT optical system are different from each other, and
the first optical member generates the first FPN, and the second optical member generates the second FPN.

4. The OCT apparatus according to claim 1,
wherein the FPN generation optical system further generates a third FPN having a distance, which is different from the first FPN, from the zero delay position, and further generates a fourth FPN having a distance, which is different from the second FPN, from the zero delay position, and the computation controller is configured to:
acquire the first correction information based on the first FPN and the third FPN, which are detected in the case of the first sweep frequency; and
acquire the second correction information based on the second FPN and the fourth FPN, which are detected in the case of the second sweep frequency.

5. The OCT apparatus according to claim 4,
wherein the computation controller is configured to:
acquire the first correction information based on difference information between mapping information of a wavenumber component based on the first FPN and mapping information of a wavenumber component based on the third FPN; and
acquire the second correction information based on difference information between mapping information of a wavenumber component based on the second FPN and mapping information of a wavenumber component based on the fourth FPN.

6. The OCT apparatus according to claim 1, further comprising:
an interception member that intercepts irradiation of the measurement light on a subject eye,
wherein the computation controller is configured to acquire the first correction information and the second correction information, based on the first FPN and the second FPN detected by the second detector in a state where the interception member intercepts the irradiation of the measurement light on the subject eye.

7. The OCT apparatus according to claim 1,
wherein the OCT apparatus executes any one of a first imaging mode for imaging the subject eye in a predetermined range and a second imaging mode for imaging the subject eye in a range different from the predetermined range,
in a case where the first imaging mode is executed, the wavelength sweep light source sweeps a wavelength at the first sweep frequency, and
in a case where the second imaging mode is executed, the wavelength sweep light source sweeps a wavelength at the second sweep frequency.

* * * * *